(12) United States Patent
Lim et al.

(10) Patent No.: US 11,814,647 B2
(45) Date of Patent: *Nov. 14, 2023

(54) METHODS OF MODULATING CELL PHENOTYPE BY WAY OF REGULATING THE GASEOUS ENVIRONMENT

(71) Applicant: XCELL BIOSCIENCES, INC., San Francisco, CA (US)

(72) Inventors: James Lim, Oakland, CA (US); Bruce Adams, Oakland, CA (US); Zack Pappalardo, San Francisco, CA (US); Brian Feth, San Francisco, CA (US)

(73) Assignee: XCELL BIOSCIENCES, INC., San Francisco, CA (US)

( * ) Notice: Subject to any disclaimer, the term of this patent is extended or adjusted under 35 U.S.C. 154(b) by 204 days.

This patent is subject to a terminal disclaimer.

(21) Appl. No.: 17/213,728

(22) Filed: Mar. 26, 2021

(65) Prior Publication Data
US 2021/0214679 A1 Jul. 15, 2021

Related U.S. Application Data

(62) Division of application No. 16/955,234, filed as application No. PCT/US2018/066197 on Dec. 18, 2018, now Pat. No. 11,365,390.

(60) Provisional application No. 62/607,586, filed on Dec. 19, 2017.

(51) Int. Cl.
C12N 5/0735 (2010.01)
C12M 1/00 (2006.01)
G01N 33/50 (2006.01)

(52) U.S. Cl.
CPC .......... *C12N 5/0606* (2013.01); *C12M 41/14* (2013.01); *G01N 33/5023* (2013.01)

(58) Field of Classification Search
None
See application file for complete search history.

(56) References Cited

U.S. PATENT DOCUMENTS

| 9,857,360 | B2 | 1/2018 | Lim et al. |
| 2002/0058019 | A1 | 5/2002 | Berenson et al. |
| 2005/0282208 | A1 | 12/2005 | Adams et al. |
| 2013/0102025 | A1 | 4/2013 | Davis et al. |
| 2014/0273211 | A1 | 9/2014 | Slukvin et al. |
| 2014/0286910 | A1 | 9/2014 | Tankovich et al. |
| 2014/0287509 | A1 | 9/2014 | Sharei et al. |
| 2014/0370598 | A1 | 12/2014 | Colton et al. |
| 2015/0010517 | A1 | 1/2015 | Chapman |
| 2016/0113968 | A1 | 4/2016 | Hung |
| 2016/0193605 | A1 | 7/2016 | Sharei et al. |
| 2016/0222353 | A1 | 8/2016 | Yang et al. |
| 2016/0251620 | A1 | 9/2016 | Gobbi |
| 2016/0289635 | A1 | 10/2016 | Sasai et al. |
| 2017/0007677 | A1 | 1/2017 | Ueda |
| 2017/0009204 | A1 | 1/2017 | Gerecht et al. |
| 2017/0105984 | A1 | 4/2017 | Saya et al. |
| 2017/0114316 | A1 | 4/2017 | Newstrom et al. |
| 2017/0121677 | A1 | 5/2017 | Colton et al. |
| 2017/0130198 | A1 | 5/2017 | Tyvoll et al. |
| 2017/0369904 | A1 | 12/2017 | Lim et al. |
| 2018/0066223 | A1 | 3/2018 | Lim et al. |
| 2018/0100134 | A1 | 4/2018 | Lim et al. |

(Continued)

FOREIGN PATENT DOCUMENTS

| EP | 2948776 | 12/2015 |
| EP | 3283611 A1 | 2/2018 |
| WO | WO-2009135206 A1 | 11/2009 |

(Continued)

OTHER PUBLICATIONS

Clarke et al. "Low Oxygen Enhances Primitive and Definitive Neural Stem Cell Colony Formation by Inhibiting Distinct Cell Death Pathways", STem Cells, 27: 1879-1886. (Year: 2009).*
Winkler et al. "Positioning of bone marrow hematopoietic and stromal cells relative to blood flow in vivo: serially reconstituting hematopoietic stem cells reside in distinct nonperfused niches", Blood, vol. 116(3): 375-385. (Year: 2010).*
Butcher et al. A tense situation: forcing tumour progression, Nat Rev Cancer. Feb. 2009, 9(2):108-122. doi:10.1038/nrc2544.
Carey et al. Mechanobiology of tumor invasion: engineering meets oncology, Crit Rev Oncol Hematol, Aug. 2012, 83(2):170-183.
Co-pending U.S. Appl. No. 16/567,618, inventor James; Lim, filed Sep. 11, 2019.
Co-pending U.S. Appl. No. 17/077,222, inventors Limjames et al., filed Oct. 22, 2020.
Frizzell, et al., Role of heterogeneous cell population on modulation of dendritic cell phenotype and activation of CD8 T cells for use in cell-based immunotherapies. Cell immunol. Jan. 2017; 311: 54-62.

(Continued)

*Primary Examiner* — Teresa E Knight
(74) *Attorney, Agent, or Firm* — Wilson Sonsini Goodrich & Rosati

(57) ABSTRACT

Embodiments of a method of modulating a potency level phenotype of a source population of cells include culturing the source cell population in a liquid medium within a cell culture incubator, the incubator is configured to independently regulate one or more variable parameters of gaseous conditions within the incubator, the more than one variable atmospheric parameters within the incubator being regulated independently of each other and independently of ambient external gaseous conditions. The method further includes regulating the one or more variable parameters of the gaseous condition within the incubator such that at least one of the one or more variable parameter differs from an ambient level of the respective variable parameter, and as a consequence of such difference from ambient conditions, the subset population is driven from a first potency level phenotype to a second potency level phenotype. In these method embodiments, the first phenotype of the subset cell population is expressed under a gaseous condition absent the regulation of the one or more variable parameters of the gaseous condition, and the second phenotype of the subset cell population is expressed as a consequence of exposure to the gaseous condition as determined by the regulation of the two or more parameters of the gaseous conditions within the incubator.

19 Claims, 29 Drawing Sheets

(56) References Cited

U.S. PATENT DOCUMENTS

2018/0267025 A1  9/2018  Lim
2020/0354674 A1  11/2020  Lim et al.

FOREIGN PATENT DOCUMENTS

| WO | WO-2010099539 A1 | 9/2010 |
| WO | WO-2014117021 A2 | 7/2014 |
| WO | WO-2016064757 A1 | 4/2016 |
| WO | WO-2016070136 A1 | 5/2016 |
| WO | WO-2016077761 A1 | 5/2016 |
| WO | WO-2016115179 A1 | 7/2016 |
| WO | WO-2016168687 A1 | 10/2016 |
| WO | WO-2017008063 A1 | 1/2017 |
| WO | WO-2017041051 A1 | 3/2017 |
| WO | WO-2017058838 A1 | 4/2017 |
| WO | WO-2017070337 A1 | 4/2017 |
| WO | WO-2017123663 A1 | 7/2017 |
| WO | WO-2017172638 A1 | 10/2017 |
| WO | WO-2017192785 A1 | 11/2017 |
| WO | WO-2017223199 A1 | 12/2017 |
| WO | WO-2019126146 A1 | 6/2019 |

OTHER PUBLICATIONS

PCT/US2018/066197 International Search Report and Written Opinion dated Mar. 15, 2019.

Powers et al., Accurate control of oxygen level in cells during culture on silicone rubber membranes with application to stem cell differentiation. American Institute of Chemical Engineers, vol. 26, No. 3, 2009: 805-818.

Salvagiotto et al. A Defined, Feeder-Free, Serum-Free System to Generate In Vitro Hematopoietic Progenitors and Differentiated Blood Cells from hESCs and hiPSCs, PLoS One, Mar. 2011, 6(3):e17829, 9 pages.

Schwartz et al. Exposure of Human Vascular Endothelial Cells to Sustained Hydrostatic Pressure Stimulates Proliferation Involvement of the $\alpha V$ Integrins, Circ Res, 1999, 84:315-322.

Sullivan et al. Hypoxia-induced resistance to anticancer drugs is associated with decreased senescence and requires hypoxia-inducible factor-1 activity, Mol Cancer Ther Jul. 2008, 7(7):1961-73.

Takahashi, et al. A developmental framework for induced pluripotency. The Company of Biologist 2015, 142, pp. 3274-3285.

Wang et al. Targeting HIF1$\alpha$ eliminates cancer stem cells in hematological malignancies. Cell Stem Cell 8(4):399-411 (2011).

* cited by examiner

METHODS OF MODULATING CELL PHENOTYPE BY WAY OF REGULATING THE GASEOUS ENVIRONMENT

CROSS REFERENCE

This application is a Divisional of U.S. application Ser. No. 16/955,234 filed Jun. 18, 2020, which is a National Stage Entry of PCT/US18/66197, filed Dec. 18, 2018, which claims priority to U.S. Provisional Application No. 62/607,586, filed on Dec. 19, 2017, each of which is incorporated herein by reference.

TECHNICAL FIELD

This application is directed to technologies for developing particular types of cell populations and expanding them for research, diagnostic, drug screening, or therapeutic purposes. In particular, the technologies relate to methods of modulating cell potency-level phenotypes, and aspects of the regulation of atmospheric variables that can contribute to implementation of these methods.

BACKGROUND

The use of cells, such as immune system cells, tumor cells, and stem cells, for research, diagnostic, drug screening, or therapeutic purposes therapeutic purposes is an accelerating area of interest, and accordingly, there is a need for methods to isolate and expand high quality cell populations for these purposes. With particular regard to stem cells and their therapeutic potential, it is well appreciated that there are ways to influence the progression of a cell lineage potency status either from the pluripotent or nearly pluripotent status of a stem cell toward an intermediately differentiated or fully differentiated state, or alternatively, to drive a cell lineage from a differentiated state toward a pluripotent state. It is known that in vitro conditions, such as the presence of any of a multitude of reprogramming factors, induction factors, growth factors, and cytokines can promote movement of a cell lineage in the directions of either increasing differentiation or (oppositely) increasing potency.

Movement of a cell lineage in either a more differentiated state or a less differentiated state is typically characterized by some aspect of the cell lineage phenotype, i.e., any observable feature that can be differentially expressed by a single genotype. Observable features associated with differences that manifest, for example, as cell morphology, dimension, adherent properties, electrical properties, metabolic activity, or migratory behavior. On another level, phenotypic differences associated with a difference in potency level can manifest as difference in messenger RNA expression of the cellular genome, or rates of protein transcription from expressed RNA.

It is known that physical factors, such as availability various substrates, or 3D scaffolding arrangement can have important influences on cellular phenotypic expression, as for example, can be manifested by cell morphology or function. And it is still further known that environment of cells in the body is often not that of the ambient conditions typical within a conventional cell culture incubator, wherein the oxygen level and the total gas pressure levels are ambient. In contrast, local compartments in the body are commonly hypoxic and/or hyperbaric. Hypoxia is known as an influencing atmospheric factor with a host of effects of particular types of cells, as significantly mediated by hypoxia-inducible factors. The effects of total atmospheric pressure on cells are less well understood than the effects of hypoxia, at least in part because it is relatively easy to create different levels of oxygen in an in vitro environment, but there are few available incubator options that can controllably vary the internal atmospheric pressure.

Thus, in addition to physical or structural aspects of the environment, gaseous or atmospheric conditions, and associated dissolved gas levels in liquid medium may also be important in driving changes in the phenotypic state of cells in culture. Understanding aspects of these relationships, as disclosed herein, may be important in the development of commercial and clinical applications of cell technologies, such as stem cell-based therapies or immunotherapies.

INCORPORATION BY REFERENCE

Each patent, publication, and non-patent literature cited in the application is hereby incorporated by reference in its entirety as if each was incorporated by reference individually.

SUMMARY

Overview of Summary

The present disclosure is directed to various methods of modulating the phenotype of cell populations, particularly the potency level phenotype, by way of regulating gaseous or atmospheric conditions within a cell culture environment, with particular attention to oxygen level and total atmospheric gas pressure. Within the body, cells are typically exposed to a fluid environment, such fluid containing dissolved gases in equilibrium with atmospheric gases at interfaces such as the lungs, or as mediated by oxygen transporting molecules. The gaseous environment to which fluids and cells within the body are exposed is one where total gas pressure is at ambient atmospheric pressure or greater simply because the body generates sites of internal pressure, and where the oxygen level is at ambient level or less, because oxygen is metabolized in the body and depleted in fluids, and there is no mechanism to increase oxygen level.

Accordingly, actual physiological conditions within the body tend to be hyperbaric and hypoxic. Embodiments of the methods provided herein relate to regulating oxygen level to hypoxic levels and regulating pressure to hyperbaric levels; to some extent therefore, embodiments of the present disclosure drive in vitro conditions toward a mimicking of particular in vivo conditions. Embodiments of the present disclosure, by way of regulating atmospheric conditions, are broadly directed toward modulating the phenotypes that cells are capable of expressing, with a particular focus on modulating aspects of phenotype related to potency.

Modulating potency level phenotype may refer either to a "downstream" movement from a state of high potency toward a more differentiated state, or alternatively, to an "upstream" movement from a relatively differentiated state toward a less-differentiated, higher potency state. Modulating potency level phenotype may also refer to stabilizing or maintaining (by way of regulating the atmospheric environment) a phenotype of a cell population that would otherwise tend to differentiate or dedifferentiate.

Modulating potency level may include operating the present disclosure, per methods disclosed herein, in conjunction with other methods of influencing phenotype-specific expression, as, by way of example, contacting cells with bioactive agents such as, by way of example, transcription factors, cytokines, or growth factors. Modulating potency level may further include causing phenotypic changes that would not occur at all, absent regulating oxygen and total atmospheric conditions, and it may include accelerating phenotypic changes that would occur anyway, albeit at a slower rate.

Cells in culture exist as populations that range from being heterogenous to homogeneous, as reflected by any criteria of interest. As cells in culture proliferate through standard cell passaging methods, populations may or may not change in terms of the relative prevalence of subpopulations that constitute the whole. When the phenotype of a population of cultured cells changes or is modulated, such modulation may occur, to varying degree, by way of the population as a whole changing, or modulation may occur by way of a particular subpopulation proliferating at a rate that is greater or lesser than other subpopulations. Accordingly, modulating the phenotype of a cell population, such as potency level phenotype, may, in some instances, by understood as modulating or changing the phenotype of a descendant population in comparison to the phenotype of the parental or source population.

Modulating Potency Level Phenotype with One or More Gaseous Parameter Variables

In a first embodiment, among several embodiments provided herein, an embodiment of a method of modulating a cellular potency level phenotype of at least a subset population of a source population of cells includes culturing the source cell population in a liquid medium within a cell culture incubator, the incubator being configured to regulate one or more variable parameters of gaseous conditions within the incubator independently of each other and independent of a corresponding ambient condition. Embodiments of the method include regulating the one or more variable parameters of the gaseous condition within the incubator such that at least one of the one or more variable parameter differs from a corresponding ambient level, and consequently driving the subset population from a first potency level phenotype to a second potency level phenotype. In these method embodiments, the first potency level phenotype of the subset cell population is that which is expressed under a gaseous condition absent the independent regulation of the two or more variable parameters of the gaseous condition, and the second potency level phenotype of the subset cell population is expressed as a consequence of exposure to the gaseous condition as determined by the independent regulation of the two or more parameters of the gaseous conditions within the incubator.

In some embodiments of the method, the cell population of a second potency level is particularly targeted as an intended product of the method. In such embodiments, the variable parameters of the gaseous conditions are selected to produce the intended product, such selection of conditions being based on any of experimental data from previous examples of a population of cells of a same type of source population or from previous examples of populations of cells similar to those of the source population.

U.S. patent application Ser. No. 15/789,464, entitled "Cancer cell enrichment system", as filed on Oct. 20, 2017, includes subject matter related regulating gas flow within a cell culture incubator, and is incorporated into herein by reference.

Pressure

In some embodiments of the present disclosure (modulating a cellular potency-level phenotype), one of the variable parameters of the gaseous conditions within the incubator is a total gas pressure, wherein the total gas pressure is greater than ambient total gas pressure. In some embodiments, the total gas pressure is greater than that of an ambient atmospheric pressure by a value in the range of about 0.1 PSI to about 10 PSI. In some embodiments, the total gas pressure is greater than that of an ambient atmospheric pressure by a value in the range of about 1 PSI to about 6 PSI. In some embodiments, the total gas pressure is greater than that of an ambient atmospheric pressure by a value in the range of about 2 PSI to about 5 PSI.

Hypoxia

In some embodiments of the present disclosure (modulating a cellular potency-level phenotype), one of the variable parameters of the gaseous conditions within the incubator is a concentration of an individual gas. In a particular embodiment, the individual gas is oxygen, wherein the level of oxygen is below ambient oxygen level. In some embodiments, the concentration of oxygen is in the range of about 0.1% to about 20%. In some embodiments, the concentration of oxygen is in the range of about 1% to about 16%. In some embodiments, the concentration of oxygen is in the range of about 2% to about 10%.

Two or More Gaseous Parameter Variables

In some embodiments of the present disclosure (modulating a cellular potency-level phenotype), the incubator is configured to regulate two or more variable parameters of a gaseous condition within the incubator independently of an ambient gaseous condition, and configured to regulate the two or more variables of a gaseous condition independently of each other. In such embodiments, one of the two variable parameters may include a total gas pressure and the second of the two variable parameters may include an oxygen level.

Two or More Gaseous Variables Varying Over the Course of the Culture Duration

In some embodiments of the present disclosure (modulating a cellular potency-level phenotype), the two or more variable parameters of the gaseous or atmospheric conditions include a total gas pressure and a concentration of at least one individual gas, and culturing the cells within a cell culture incubator includes culturing for a culture duration over which time both the total gas pressure and the concentration of the at least one gas is substantially constant. In other embodiments of the present disclosure, the two or more variable parameters of the gaseous conditions include a total gas pressure and a concentration of at least one individual gas, wherein culturing the cells within a cell culture incubator includes varying at least one of the total gas pressure or the concentration of the at least one gas over a culture duration.

In some embodiments of the present disclosure, varying at least one of the total gas pressure and the at least one individual gas during the culture duration may include any of increasing or decreasing any one or more of the total gas pressure and the concentration of the at least one individual gas during the culture duration. In some embodiments, varying any one or more of the total gas pressure and the concentration of the at least one individual gas may include varying as a ramping function. In some embodiments, varying any one or more of the total gas pressure and the concentration of the at least one individual gas may include varying as a step function.

In some of these embodiments, varying any one or more of the total gas pressure and the concentration of the at least one individual gas may include culturing under a first set of gaseous conditions and culturing under at least a second set of gaseous condition. In some embodiments, culturing under a first gaseous condition and culturing under at least a second gaseous condition may include moving from the first condition to the at least second condition and back to the first condition one or more times.

In some of these embodiments, varying any one or more of the total gas pressure and the at least one individual gas may include changing the total gas pressure and the concentration of the at least one gas synchronously. In some embodiments, varying any one or more of the total gas pressure and the at least one individual gas may include changing the total gas pressure and the concentration of the at least one gas asynchronously.

Modulating a Potency Level Aspect of the Phenotype

In some embodiments of the present disclosure (modulating a cellular potency-level phenotype), modulating the potency level phenotype includes any of driving the subpopulation toward a state of greater differentiation (or lesser potency) or toward a state of greater potency (or lesser differentiation).

Moving a High Potency Level Cell Toward a Differentiated Phenotype

In particular embodiments of the present disclosure, modulating the potency level aspect of the phenotype of the subset population of cultured cells includes driving the cells from a state of high potency level toward a state of a mature, differentiated cell phenotype. In some of these embodiments of the present disclosure, modulating a potency level phenotype includes driving a cell having a pluripotent phenotype toward a cell type belonging to any of the embryonic germ layer derivatives, said germ layers consisting or endoderm, mesoderm, and ectoderm.

Neural Cells and Cardiac Myocytes

In some embodiments of the present disclosure, driving a potency level phenotype toward an ectodermal derived cell type includes driving the phenotype toward that of an epidermal or neural cell type.

Intermediately Differentiated or Progenitor Cell Type

In some embodiments of the present disclosure, modulating a potency level phenotype includes driving a cell having a pluripotent phenotype toward that of an intermediately differentiated or progenitor cell phenotype. In some of these embodiments, the intermediately differentiated cell phenotype includes a neural phenotype. In particular examples of these embodiments, the neural phenotype is characterized by expression of any one or more of oligodendrocyte transcription factor OLIG-2, PAX6, NESTIN, and SOX2. In another example of an embodiment, the intermediately differentiated cell phenotype includes a cardiomyocyte progenitor phenotype.

In another embodiment, driving a potency level phenotype toward a state of a mature, differentiated cell type includes driving a population human induced pluripotent cells (iPSCs) toward a myeloid progenitor cell type, as indicated by emergence of CD34+CD45+CD43+ cells.

Fully Differentiated Cell Type

In some embodiments of the present disclosure, modulating a potency level phenotype includes driving a cell having an intermediately differentiated cell phenotype toward that of a cell having a fully differentiated cell phenotype. By way of example an intermediately differentiated cell phenotype may include a neural cell phenotype and a mature differentiated call phenotype may include a neuronal phenotype.

In some of these embodiments, an intermediately differentiated cell phenotype is a neural progenitor cell phenotype and a mature differentiated cell phenotype is a neuronal cell phenotype, the method may further include adding a neurotrophic factor to the liquid medium. In some of these embodiments, a neural progenitor phenotype may be characterized by expression of any of PAX6, SOX2, or NES. In some of these embodiments, a neural progenitor phenotype may be characterized by expression of any of neurosphere formation, neurofilament expression, synapsin expression, or neural functional activity. In some of these embodiments, the neuronal cell phenotype may be characterized by expression of any of ChAT (choline acetyltransferase) and neurofilament H. In some of these embodiments, an intermediately differentiated cell phenotype includes a neural progenitor cell phenotype and a mature differentiated call includes an astrocytic phenotype.

Moving a Differentiated Cell Toward a High Potency Level Phenotype and Use of Transfection In some embodiments of the present disclosure, modulating the potency level aspect of the phenotype of the subset population of cultured cells includes driving the cells from a differentiated state toward a state of higher potency (thus an "upstream" movement). In some of these particular embodiments, driving the cells from a differentiated state toward a state of higher potency includes reprogramming the genome of the differentiated cell into a less epigenetically modified state.

In some embodiments of the present disclosure, modulating a differentiation phenotype includes driving a cell having differentiated cell phenotype toward an induced pluripotent stem cell (iPSC) phenotype. In some of these particular embodiments, driving a cell having a differentiated cell phenotype toward an induced pluripotent stem cell (iPSC) phenotype includes transfecting the cell with one or more transcription factors. In some of these particular embodiments, the one or more transcription factors include a member of the Oct-3/4 family, a member of the Sox family, a member of the Klf family, a member of the Myc family, or a member of GLIS-1 family.

Moving a Differentiated Cell (Fibroblast) Toward a High Potency Level Phenotype, and Thence to a Third and More Differentiated Phenotype Some embodiments of the present disclosure further include modulating the second potency level phenotype such that it becomes a third potency level phenotype. In some of these particular embodiments, the first potency level phenotype includes a fibroblast derived from a patient, and wherein the second potency level phenotype includes that of a reprogrammed pluripotent cell, and wherein the third potency level phenotype includes an intermediately differentiated cell type. Some of these particular embodiments include modulating the third potency level phenotype such that it becomes a fourth potency level phenotype, corresponding to that of a mature, differentiated cell type.

In some of these embodiments, the gaseous condition that drives the cell population from the second potency level phenotype to third potency level phenotype is substantially the same as the gaseous condition that drives the cell population from the third potency level phenotype to the fourth potency level phenotype. And in other embodiments, the gaseous condition that drives the cell population from the third potency level phenotype to fourth potency level phenotype is different than the gaseous condition that drives the cell population from the second potency level phenotype to the third potency level phenotype.

In some of these embodiments, the gaseous condition that drives the cell population from the first potency level phenotype to second potency level phenotype is different than the gaseous condition that drives the cell population from the second potency level phenotype to the third potency level phenotype. And in some of these embodiments, the gaseous condition that drives the cell population from the first potency level phenotype to second potency level phenotype is substantially the same as the gaseous conditions that drives the cell population from the second potency level phenotype to the third potency level phenotype.

Biomarkers as Indication of Potency Level Phenotype or Differentiation State

In some embodiments of the present disclosure, modulating the potency level phenotype includes modulating an expression of a differentiation marker, the marker reflecting any or more of gene expression, protein expression, cellular functionality, kinetic property, or metabolic pathway activity of at least the subset population of the cultured population of primary cells. Markers, sometimes referred to as "biomarkers", as used herein, are typically proteins that distinguish one type of cell from another; these "marker" proteins are typically made visible or detectable by antibody-based procedure. In particular embodiments, the differentiation marker includes a pluripotency marker. In some of these particular embodiments, the pluripotency marker includes any one or more of Nanog, Oct4, and Sox2.

In some embodiments of the present disclosure, the differentiation marker includes a neural cell marker. Such a neural cell marker may include any one or more of synapsin 1, ChAT, neurofilament H, or NES.

In some embodiments of the present disclosure, the cell population is presumed to include neural cells, and measuring a level of an expression of at least one differentiation state marker includes measuring the level of one or more neural cell markers, such as PAX6.

In some embodiments of the present disclosure, modulating a state of potency-level phenotype includes modulating an expression of an aspect of cell morphology, dimension, adherent properties, migratory behavior, electrical, or activation properties of at least the subset population of the cultured population of primary cells. In some of these embodiments, an expression of an aspect of cell morphology, dimension, adherent properties, migratory behavior, electrical, or activation properties of at least the subset population of the cultured population of primary cells is observed by way optical methods or by way of measuring electrical properties.

Other Aspects of the Culture Conditions

In some embodiments of the method, the liquid medium may include one or more cell differentiation induction factors or growth factors. By way of example, the cell differentiation induction and growth factors may include a neural induction factor, and by way of further example, such as any one or more of BDNF and GDNF.

In some embodiments of the present disclosure, the liquid medium is a chemically defined and is absent animal-derived components.

In some embodiments of the present disclosure, the cell culture incubator is configured to accommodate one or more cell culture vessels exposed to the gaseous conditions within the incubator, the one or more cell culture vessels accommodating the liquid medium. And in some of these embodiments, the one or more cell culture vessels each include an internal surface and one or more cell-binding substrates disposed on the internal surface.

Expanding the Subset Population that is Expressing the Second Phenotype

Some embodiments of the present disclosure may further include isolating cells of the second potency level phenotype, and expanding a population of cells of the second potency level phenotype by way of further cell culturing. In a particular embodiment, wherein a particular second potency level phenotype is desired, and wherein a set of the two or more independently regulated parameters of the gaseous conditions that favor an expression of the desired second potency level phenotype has been determined, the method may further include expanding the cultured subset of cells of expressing the second potency level phenotype by a culturing under those independently regulated gaseous conditions.

Cohort Cultures

Some embodiments of the present method may be adapted to determine a gaseous condition favorable for outgrowth of a population having a desired potency level phenotype. Such a method includes splitting the source population of cells into cohort cultures comprising at least a first and a second cohort culture, and culturing the cohort cell cultures in parallel under gaseous conditions that differ only with regard for variations in any of total gas pressure and oxygen concentration. "Cohort", as used herein, simply refers to experimental groups of cultures that are identical (all from a common source) at the outset of culturing under various different atmospheric conditions. This embodiment of the method may further include measuring a level of an expression of at least one marker indicative of the desired potency level phenotype within each of the cohort cultures; and based on the results of differentiation marker level measurement among the cohort cultures, determining which of the variations in gaseous conditions is optimal for the outgrowth of the cell population having the desired potency level phenotype.

Modulating Phenotype with One or More Gaseous Parameter Variables

In another embodiment, among several embodiments provided herein, an embodiment of a method of modulating a cellular phenotype of at least a subset population of a source population of cells includes culturing the source cell population in a liquid medium within a cell culture incubator, the incubator being configured to regulate one or more variable parameters of gaseous conditions within the incubator independently of each other and independent of a corresponding ambient condition. Embodiments of the method include regulating the one or more variable parameters of the gaseous condition within the incubator such that at least one of the one or more variable parameter differs from a corresponding ambient level, and consequently driving the subset population from a first phenotype to a second phenotype. In these method embodiments, the first phenotype of the subset cell population is that which is expressed under a gaseous condition absent the independent regulation of the two or more variable parameters of the gaseous condition, and the second phenotype of the subset cell population is expressed as a consequence of exposure to the gaseous condition as determined by the independent regulation of the two or more parameters of the gaseous conditions within the incubator.

BRIEF DESCRIPTION OF THE FIGURES

Schematic Diagrams

FIG. 3A is a schematic diagram of the experimental design.

FIG. 3B shows an unsupervised hierarchical clustering of cumulative differentially expressed genes (763 total) by whole-transcriptome RNA-seq at passage 7 in the indicated O2 and PSI values.

FIG. 3C is a Venn diagram that shows significant differentially expressed genes (as shown in FIG. 3B) showing overlap between analysis groups.

FIG. 3D shows the top five gene ontology (GO) terms for both up-regulated and down-regulated differentially expressed genes between 15% O2+2 PSI vs. 15% O2+0 PSI. Gene ontology enrichment is ranked according to adjusted p-value of the false discovery rate (FDR) and displayed on log 10 scale. The number of significant differentially expressed genes for each GO term is displayed in the bar graph.

FIG. 3E shows representative immunofluorescence and phase contrast images of passage 7 iPSCs showing expression of markers PAX6 and NES in the indicated culture conditions.

FIG. 3F shows flow cytometry data of psa-NCAM stained iPSCs at passage 7 cultured in 15% O2+0 PSI (light histogram) and 15% O2+2 PSI (dark histogram). The summary of the % psa-NCAM positive (+) cells is shown in the column graph on the right. Gating of psa-NCAM positive cells was performed using un-stained iPSCs.

FIG. 3G shows representative immunofluorescence images of passage 7 iPSCs showing expression of markers POU5F1, NANOG, and SOX2 in the indicated culture conditions.

FIG. 3H shows pluripotency and germ layer differentiation marker gene expression from DEseq2 log 2 fold changes between both 15% O2+2 PSI vs. 15% O2+0 PSI (blue bars) and 5% O2+2 PSI vs. 5% O2+0 PSI (red bars) iPSC lines.

FIG. 4A shows unsupervised hierarchical clustering of differentially expressed genes (1473 total) by whole-transcriptome RNA-seq at passage 3 with adjusted FDR between 15% O2+2 PSI vs. 15% O2+0 PSI using DEseq2. n=3 independent donor iPSC lines, two from human fibroblast (iPSC lines 1 and 2) and one from human CD34+ cord blood (iPSC line 3) cells.

FIG. 4B is a Venn diagram of showing significant differentially expressed genes from (FIG. 1A) and additionally, differentially expressed genes between 5% O2+0 PSI vs. 5% O2+2 PSI.

FIG. 4C shows representative immunofluorescence images of passage 3 iPSCs showing expression of POU5F1 and NANOG in the indicated culture conditions.

FIG. 4D shows naïve/Primed associated genes and epigenetic regulator gene expression from DEseq2 log 2 fold changes between both 15% O2+2 PSI vs. 15% O2+0 PSI (dark bars) and 5% O2+2 PSI vs. 5% O2+0 PSI (light bars) iPSC lines. All 15% O2+2 PSI vs. 15% O2+0 PSI (blue bars) have adjusted p-value (FDR)<0.05, and those gene names with a black dot are also significant for 5% O2+2 PSI vs. 5% O2+0 PSI (red bars).

FIG. 4E shows flow cytometry analysis of iPSCs stained for the primed-state associated surface marker CD57 (B3GAT1) in the indicated culture condition. Bottom left column graph is mean fluorescence intensity (MFI, the geometric mean) for the histograms. Bottom right column graph is the mean MFI at each time-point for all iPSC lines.

FIG. 4F shows the top five GO terms for both up-regulated and down-regulated differentially expressed genes between 15% O2+2 PSI vs. 15% O2+0 PSI. Gene ontology enrichment ranked according to adjusted p value (FDR) and displayed on log 10 scale. The number of significant differentially expressed genes for each GO term is displayed in the bar graph.

FIG. 5A Glycolysis and oxidative phosphorylation pathway-related genes from Hallmark and Kegg gene ontology databases that are differentially expressed between 15% O2+2 PSI vs. 15% O2+0 PSI with adjusted (FDR) p-value<0.05. Un-supervised hierarchical clustering of data is shown as scaled log 2 fold change across rows (genes).

FIG. 5B shows box-plots of cumulative significant differentially expressed genes from (a) with 5% O2+2 PSI vs. 5% O2+0 PSI genes included. The total number of significant genes (n) is listed above each group.

FIG. 6A shows representative immunofluorescence images and parallel flow cytometry analysis of iPSC-2 line differentiated for 6 days in medium containing 10 ng/mL recombinant LIF and NOG and stained for PAX6 and NES. Bottom column graph shows geometric mean fluorescence for the flow cytometry data for PAX6 and NES.

FIG. 6B shows representative immunofluorescence images of day 31 motor neurons differentiated from cord blood derived iPSC neural stem cells (CB iPSC-NSC) and bone marrow derived iPSC neural stem cells (BM iPSC-NSC) stained for choline acetyltransferase (ChAT, in red) and Neurofilament-H (in green). (Colors refer to original micrographs.) Scale bars=50 μM. Quantification for ChAT and neurofilament H is displayed in the column graphs to the right as of total area of staining.

FIG. 6C shows CNS-type neuronal differentiation using the same source NSC lines as in (b) stained for both MAP2 (red) and SYN1 (green) day 14 and 21 of differentiation. Scale bars=50 μM. Quantification of the mature neuronal marker SYN1 is displayed in the column graphs to the right.

For both (b) and (c), n=3 images quantified per condition. Error bars are standard error of the mean. *=p-value<0.05, **=<0.01 student's T test.

Figure 7A:
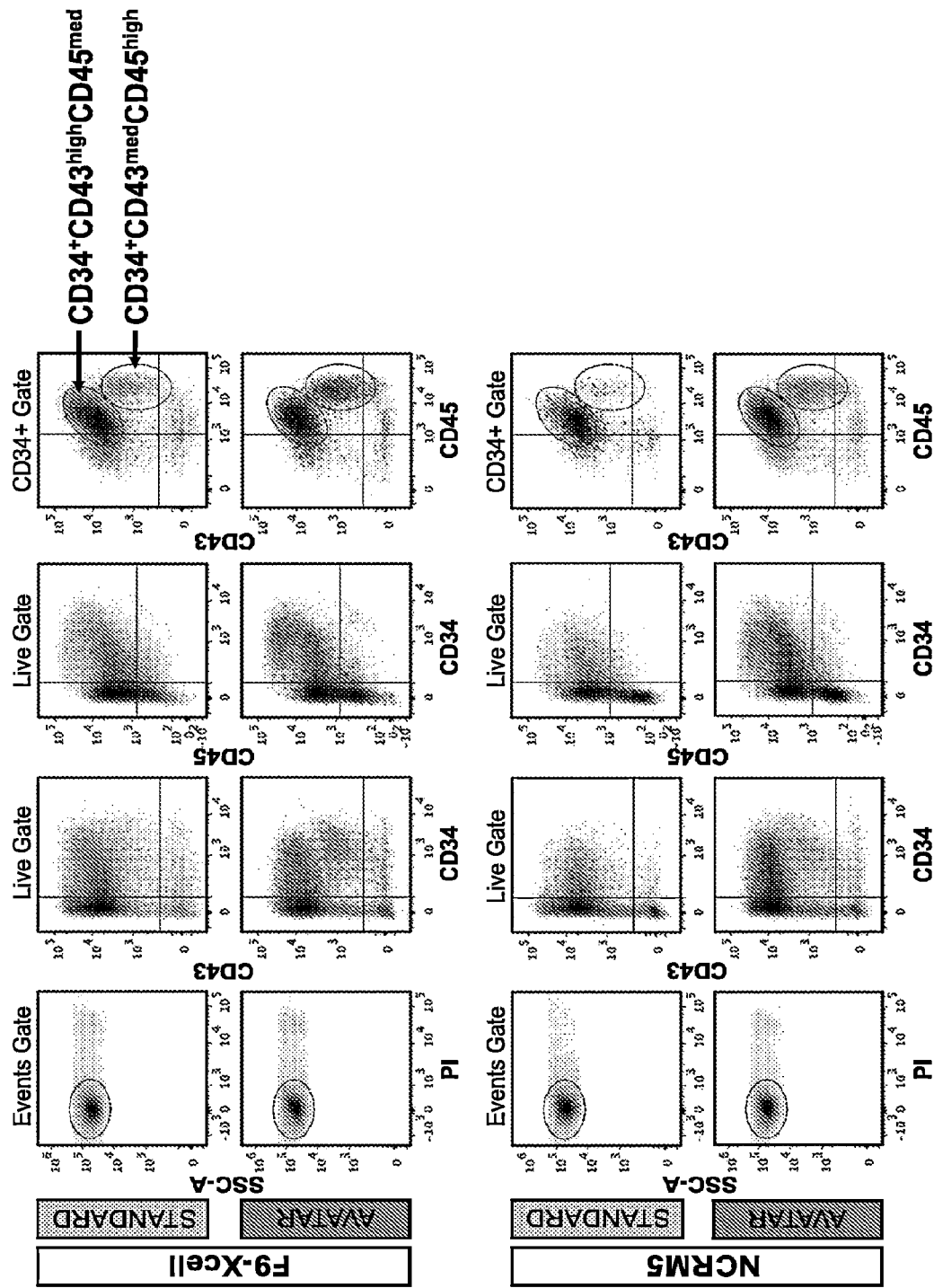
Figure 7B:
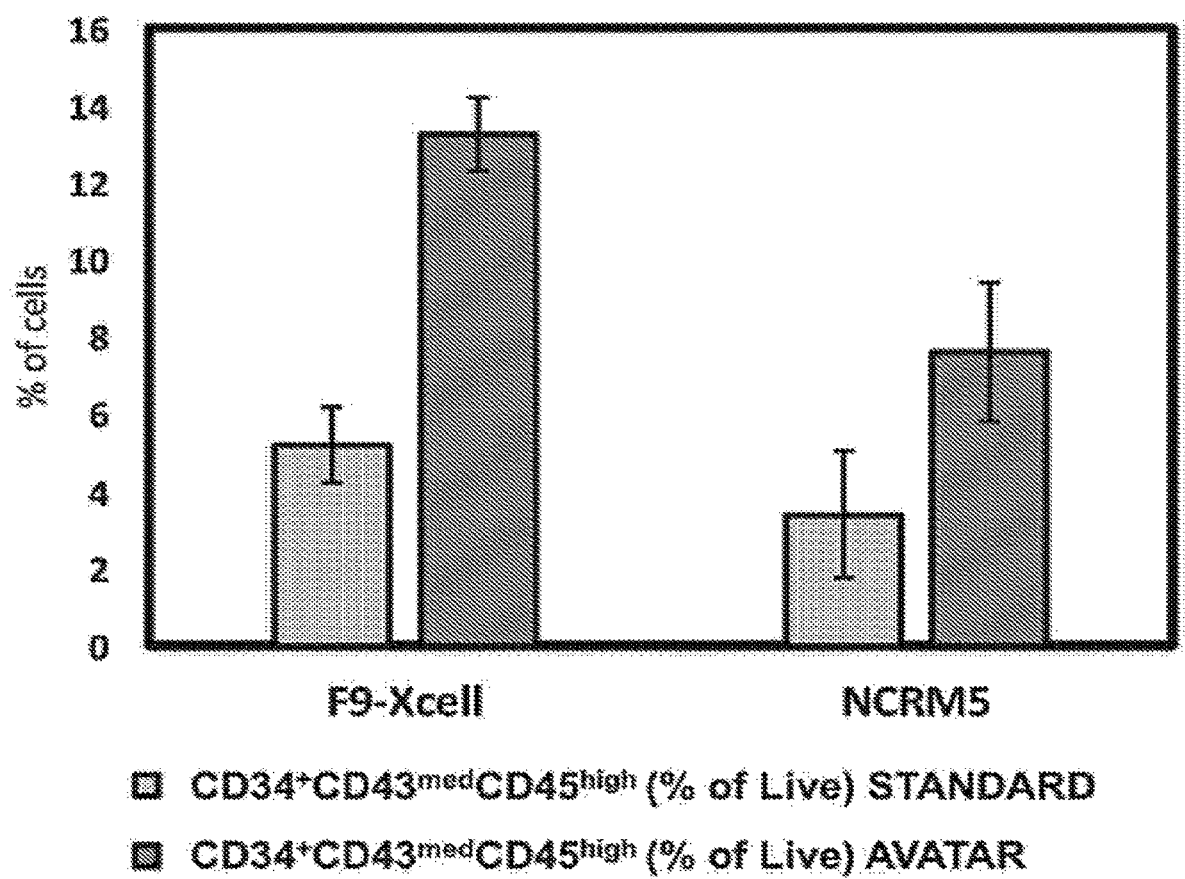

FIG. 7A-7B show data from studies of two unique donor iPSC lines, one from dermal fibroblasts (F9-Xcell) and one from CD34+ cord blood cells (NCRM5), that were cultured in 3% oxygen and elevated pressure (+2 PSI) for the first six days of differentiation in phase I medium, followed by culture in 15% oxygen and elevated pressure (+2 PSI) for a further 8 days.

FIG. 7A shows representative flow cytometry density plots for propidium iodide and SSC-A gating, CD34 and CD43 gating, CD34 and CD45 gating, and CD34, CD43, and CD45 gating. The population of cells highlighted by a circle with a check mark in the far right plot indicates CD34+CD43medCD45+ expression.

FIG. 7B is a bar graph showing mean percent of CD34+ CD43medCD45+ expressing cells for each iPSC line from the flow cytometry data of FIG. 7A. Error bars in the column graph are standard error of the mean for technical duplicates. For FIGS. 7A and 7B, "standard" refers to a conventional $CO_2$ incubator set to 5% $CO_2$, 37 degrees Celsius, and ambient oxygen.

Method Flow Diagrams

Figure 8:
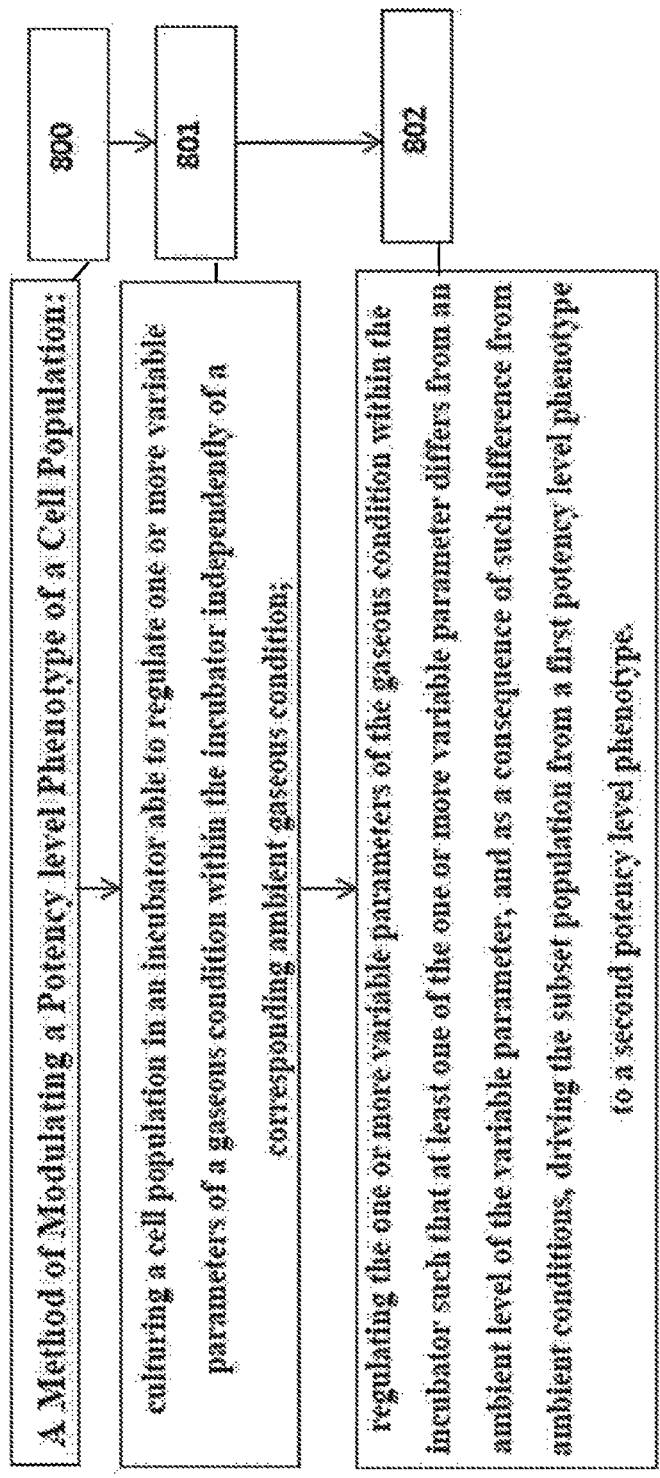

FIG. 8 is a flow diagram of an embodiment of a method of modulating the potency level phenotype of a cell population by regulating one or more variable aspects of a gaseous condition within an incubator such that these gaseous conditions differ from the corresponding ambient gaseous condition.

Figure 9:
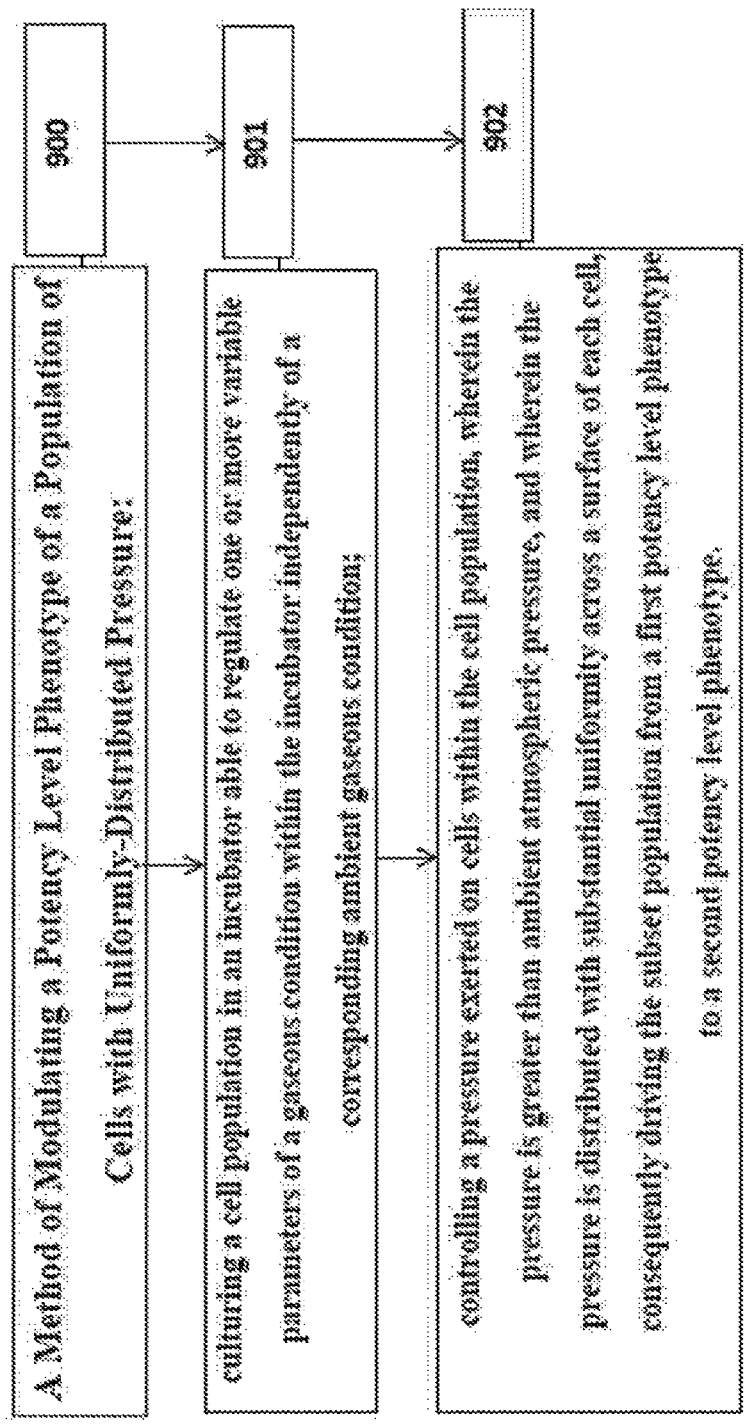

FIG. 9 is a flow diagram of an embodiment of a method of modulating the potency level phenotype of a cell population by regulating one or more variable aspects of a gaseous condition within an incubator such that these gaseous conditions differ from the corresponding ambient gaseous condition, wherein the pressure is application substantial uniformity across the cell surface.

Figure 10:
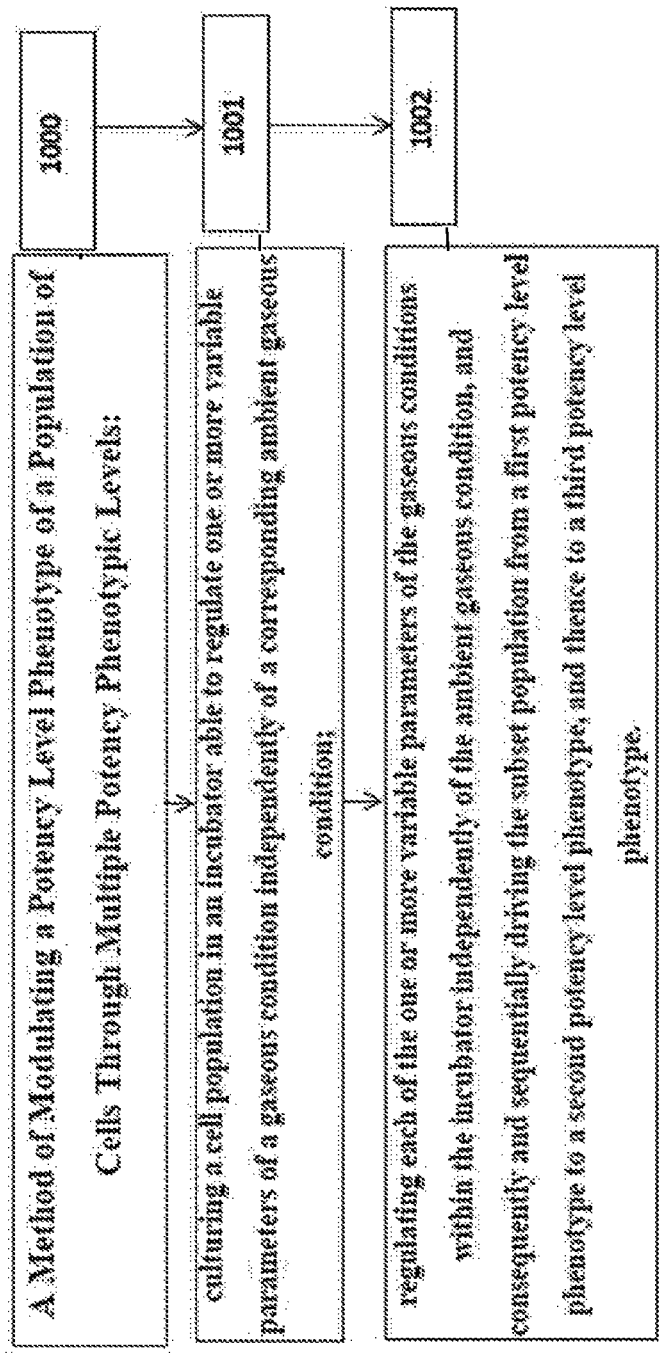

FIG. 10 is a flow diagram of an embodiment of a method of modulating the potency level phenotype of a cell population through multiple potency levels by regulating one or more variable aspects of a gaseous condition within an incubator such that these gaseous conditions differ from the corresponding ambient gaseous condition.

Figure 11:
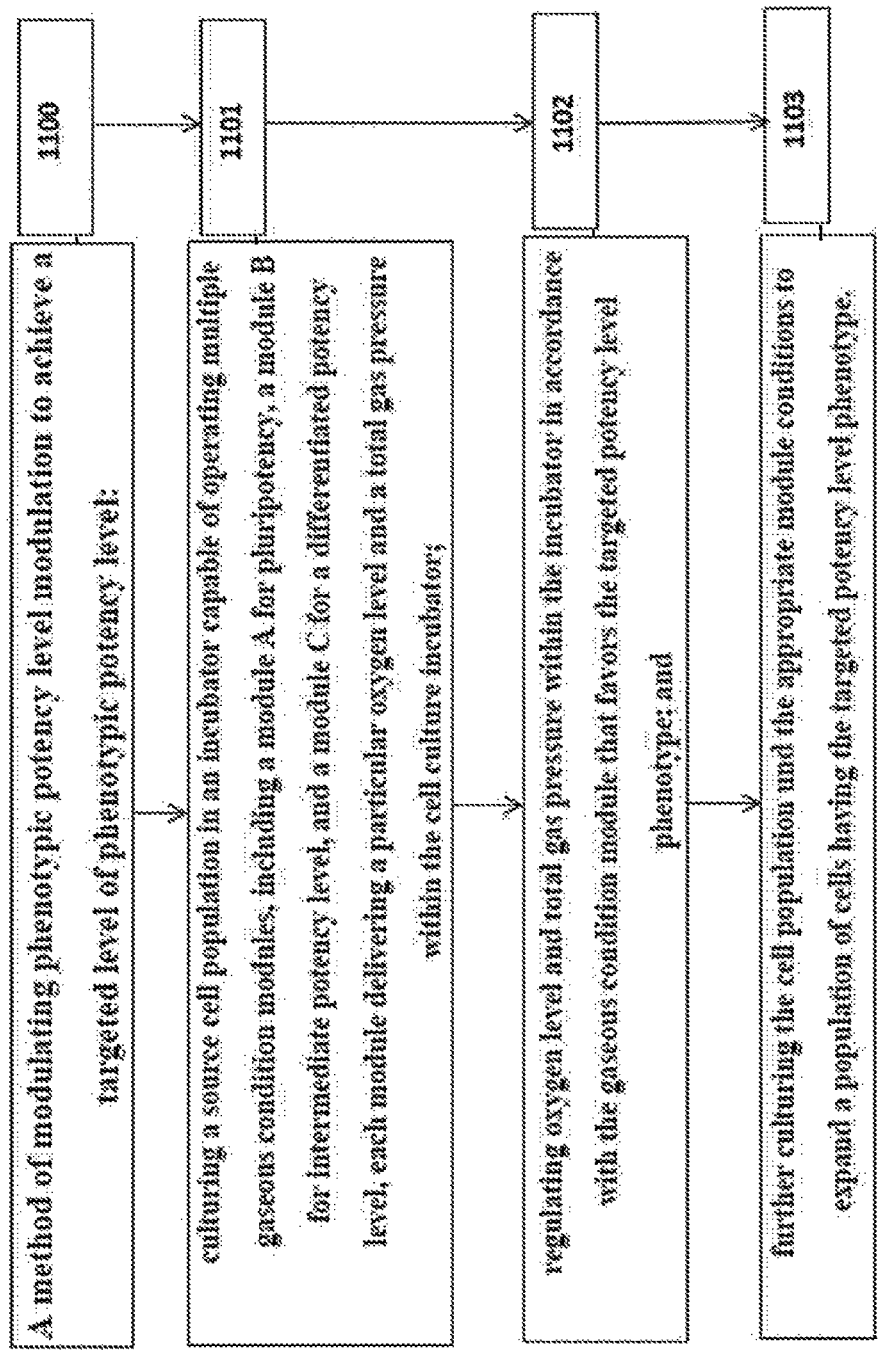

FIG. 11 is a flow diagram of an embodiment of a method of modulating the potency level phenotype of a cell population within a workflow context that may be used in a clinical manufacturing context, where an expanded cell population may be used for research, diagnostic, drug screening, or therapeutic purposes or therapeutic purposes.

Figure 12:
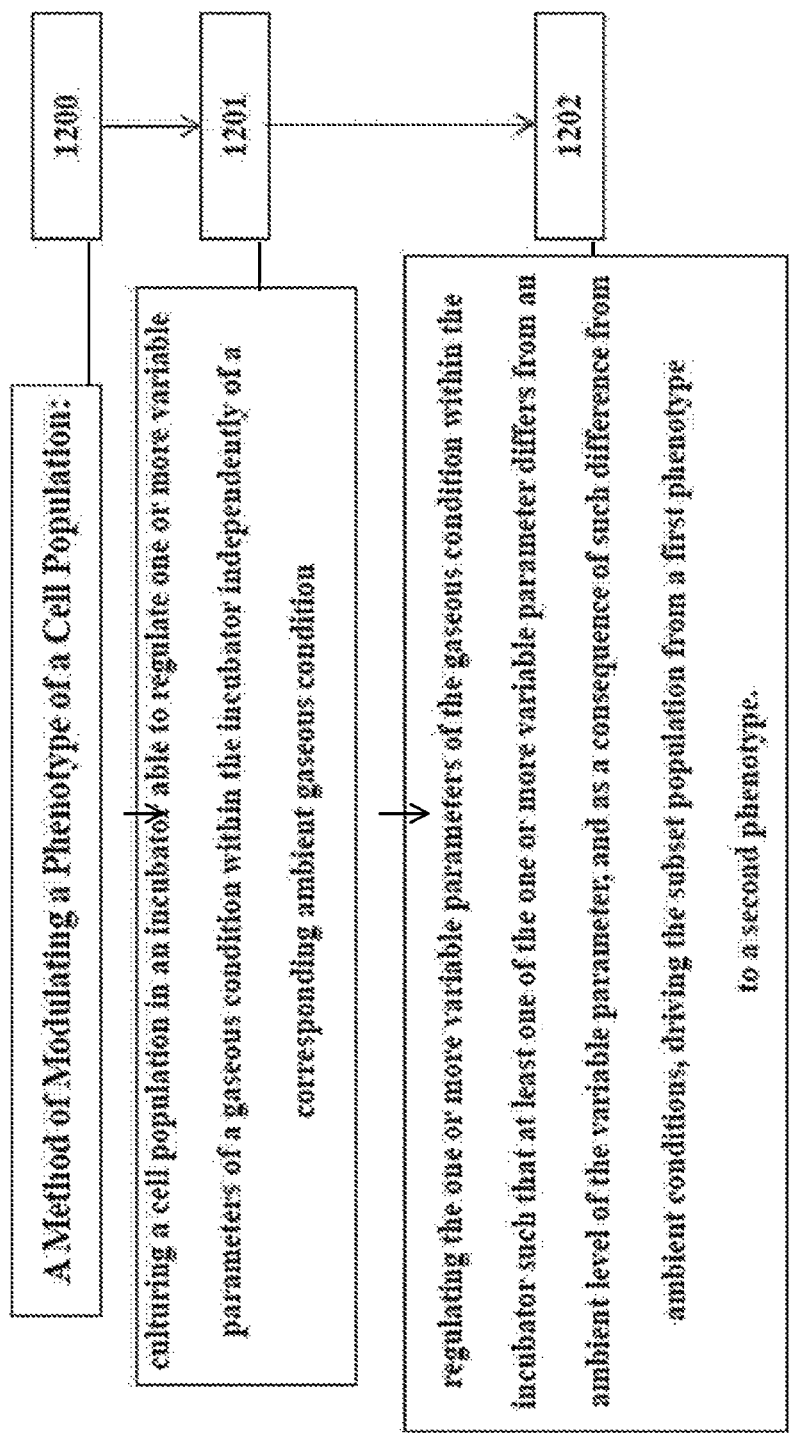

FIG. 12 is a flow diagram of an embodiment of a method of modulating the phenotype of a cell population by regulating one or more variable aspects of a gaseous condition within an incubator such that these gaseous conditions differ from the corresponding ambient gaseous condition.

DETAILED DESCRIPTION

Introduction and Terminology

Embodiments of the technology are directed to methods of modulating aspects of cellular biology by way of regulating the gaseous or atmospheric environment within a cell culture incubator. Cellular responses to manipulation of the gaseous environment, by way of example, may include the modulation of expressed cellular phenotypes with respect to cellular potency-level, particularly with regard to the continuum ranging between pluripotent and differentiated states. Regulating the gaseous environment within a cell culture incubator may be directed toward holding a particular condition in a steady state, and it may also be directed toward providing a dynamic state, in which aspects of the gaseous environment change during the course of a cell culture duration.

Gaseous environment parameters include the total atmospheric pressure as well as the partial pressure of individual gases. Of the various individual gases included in the cell culture environment, embodiments of the technology described here relate particularly to oxygen, and more particularly to low-oxygen or hypoxic conditions. Regarding total atmospheric pressure, biological responses described herein relate primarily to the effects of an atmospheric pressure that is elevated above the ambient atmospheric pressure. Total gas pressure values are typically recited in terms of the pounds/square inch (PSI), which should be understood as the PSI level above ambient atmospheric pressure.

Oxygen levels are typically referred to in terms of a concentration % value, i.e., the relative amount of oxygen present with respect to all gases present within a given volume, regardless of the summed total atmospheric pressure of all gases present. A parameter thought be more biologically relevant than "concentration %" is the partial pressure of oxygen, i.e., the amount of oxygen present per unit volume, in absolute terms, regardless of the relative presence of other gases. However, oxygen level is commonly recited as a concentration % value, and instruments typically display oxygen level as a concentration % value. Accordingly, the parameter term generally used in this application is oxygen concentration %.

In addition of regulating levels of oxygen and total gas pressure, some embodiments of methods of modulating phenotype through atmospheric means may include regulating temperature and regulating pH. Regulating pH within cell culture media with a bicarbonate buffering system is typically done by regulating the concentration of carbon dioxide in the internal atmosphere. Regulation of pH within cell culture media can also be done by way of using other buffering systems, which can mitigate some of the complexity of controlling pH solely by way of carbon dioxide gas level.

"PSI", as used herein, refers to pressure (pounds per square inch) over the ambient atmospheric pressure, whatever the ambient condition may be. It is recognized that this is a casual use of the term, and more formal language would designate it as PSIG (PSI "gauge"), however "PSI" widely in use in this informal sense, particularly in instrument dials and readouts.

As noted above, embodiments of the disclosed technology rely on an incubator that can independently regulate oxygen level and total gas pressure within the confines of a cell culture incubator chamber (see U.S. patent application Ser. No. 15/789,464, "Cancer cell enrichment system", as filed on Oct. 20, 2017). A term that incorporates both variables, the "O-P condition"; refers to a condition that is defined by the combination of the two variable atmospheric parameters (oxygen level and total gas pressure). Any terminology that defines each parameter, respectively can be used to identify the O-P condition. For example, oxygen level may be defined in terms of concentration (relative % of total gas) or partial pressure (absolute level of oxygen per unit volume). By way of a specific example, an O-P condition could be defined as "3% oxygen—3 PSI".

Cell culture "duration" or "course", as used herein, are terms that refer to a length of time during which a particular population of cells, a subpopulation of cells, a single cell, or descendants of any of the foregoing are in culture within an incubator configured to regulate the gas composition to which cells are exposed. A cell culture duration is typically at least a day, and typically can range from periods of several days, several weeks, and even several months, during which time the cultured cells can be cultured and passaged under different conditions, and be subject to one or more workflows during which cells are subjected to different sets of conditions, in various orders, to one or more particular ends.

"Phenotype", as used herein, refers to any feature of a cell that manifests as a variation in observable expression of a particular genotype, such variation arising from the state of development, differentiation, activation, or under the influence of factors within the cellular milieu. Phenotypic expression can manifest in any observable form, such as, by way of example, morphologic or structural variation, molecular variation (any class of biological molecule), metabolic, or functional or behavioral variation. Metabolic variation can manifest, by way of example, via substrate and metabolite flux through metabolic pathways or by way of rates of enzyme, receptor, ion transporter, or ion channel activity.

The various forms of phenotypic expression are broadly considered to be manifestations of control at the level of transcription of DNA into RNA, for example, as mediated by transcriptional factors or by way of epigenetic modification of DNA. "Phenotype" can be used specifically with reference to an individual cell or more generally to a cell population, where it refers to an apparent or dominant character of the population, even the cell population, in fact, may have a level of heterogeneity, harboring cells of other phenotypes.

"Potency-level phenotype" refers to a phenotypic spectrum that ranges from the totipotent character of a zygote to the substantially fixed potency of a terminally differentiated cell. Aside from a totipotent zygote, per various terminologies in use, other cell potency level phenotypes include pluripotency, multipotency, oligopotency, and unipotency. Potency-level phenotype variation is closely linked with the concept of "plasticity", i.e., a high potency level cell has a high degree of phenotypic plasticity, and a low potency or highly differentiated cell has a low degree of phenotypic plasticity. Although potency-level phenotype refers to potency in particular, variations in potency-level phenotype may also include a full range of other aspects of phenotypic variation, as listed above.

In this patent application, cells are variously described as being (a) pluripotent, (b) intermediately-differentiated or a progenitor of a particular cell type, or (c) fully differentiated or mature. A stem cell is a cell having a high potency level, such as pluripotency. An induced pluripotent stem cell (IPSC) is a cell that in a native state had at least some degree of differentiation, but by way of methods of environmental manipulation and/or transfection has gained in potency level, thus being "induced" and "pluripotent".

Cells multiply by dividing, a single parent cell giving rise to two daughter cells. Cells, as subjected to methods provided herein, typically exist within populations that may be either substantially homogenous or heterogeneous to varying degree. As cells within populations divide, the population, as a whole, can be said to be expanding. If an initial cell population is heterogeneous, including (for example) a subpopulation 1 and a subpopulation 2, expansion of the initial population may involve the expansion of subpopulation 1 at a greater rate than that of subpopulation 2. Indeed, subpopulation 1 may expand while subpopulation 2 is declining. In a scenario such as this, it can be said that resulting cell population is enriched with subpopulation 1.

Cell populations, as subjected to methods provided herein, typically are outside the body, in vitro, within a cell culture incubator. Cell culturing, thus, refers to growing or maintaining cells within an incubator. Growing cells, in this sense, refers to the expansion of cell populations by cell division, as described above. Cultured cells may also live without dividing, in which case cells can be said to be maintained in cell culture. There are many uses for expanded populations having a particular potency level phenotype, or any particularly well characterized phenotype for that matter; these include cell populations to be directed toward research, diagnostic, drug screening, or therapeutic purposes or therapeutic use.

Some terms are used in the description of the various relevant atmospheric parameters, relevant cell types, and gene expression data. Table 1 provides units and levels of variable atmospheric parameters that are regulated by embodiments of the technology. Table 2 provides a list of cell types, of varying potency level phenotypes and the cell culture modules that are included in the scope of the technology. With regard to gene expression analysis, "unsupervised hierarchical clustering" refers to grouping genes or samples such that gene similarities within the groups are greater than between groups, without any presumptive (thus "unsupervised") classification of the genes. And "gene ontology (GO) enrichment" refers to a statistical analysis of genome datasets using classification of genes and their corresponding products (RNA or protein) into groupings based on the relatedness of their biological function ("GO terms").

The whole of a cell culture environment within an incubator includes many factors, as, for example, the composition of the liquid cell culture medium and bioactive agents included therein, surfaces and structures with which cells engage, temperature, and atmospheric conditions external to the liquid. Embodiments of methods provided herein, focus on regulating the gaseous composition and the total gas pressure, as noted above in the description of the O-P (oxygen level, total atmospheric pressure) condition. The cell culture environment also includes the composition of the liquid cell culture medium, including organic and inorganic compounds, as well as particular bioactive agents. Bioactive agents are compounds that are not metabolic fuel or nutritional, but rather have biological effects that follow from their informational or directive nature, as typically mediated by physical or chemical interaction with molecules of the target cell. The cell culture environment may further include physical or chemical aspects of the surfaces that cells contact. The cell culture environment may further include any structural features with which cultured cells may interact, for example, features that provide a 3D structural context. The cell culture environment may also include interactive relationships between cells or among cell populations. The cell culture environment may further include electrical engagement of cells, for example electrical current as transmitted through the liquid medium or through solid structures which cells may contact.

Figure 1A:
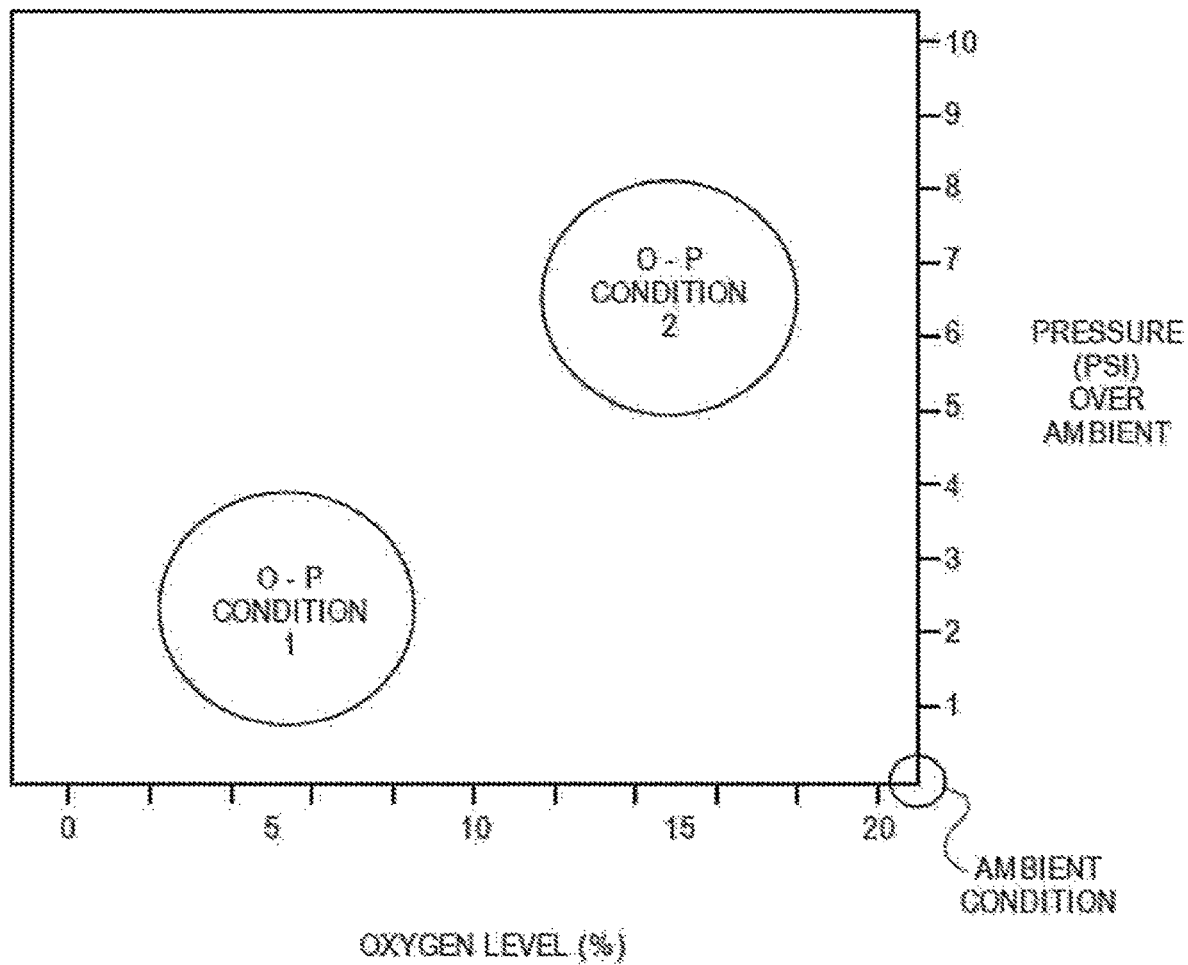
FIG. 1A is an X-Y graphic representation of an oxygen level parameter (X-axis) and a pressure level parameter (Y-axis) for gaseous conditions in a cell culture incubator, showing two particular oxygen-pressure (O-P) conditions: O-P Condition 1 and O-P Condition 2.
Figure 1B:
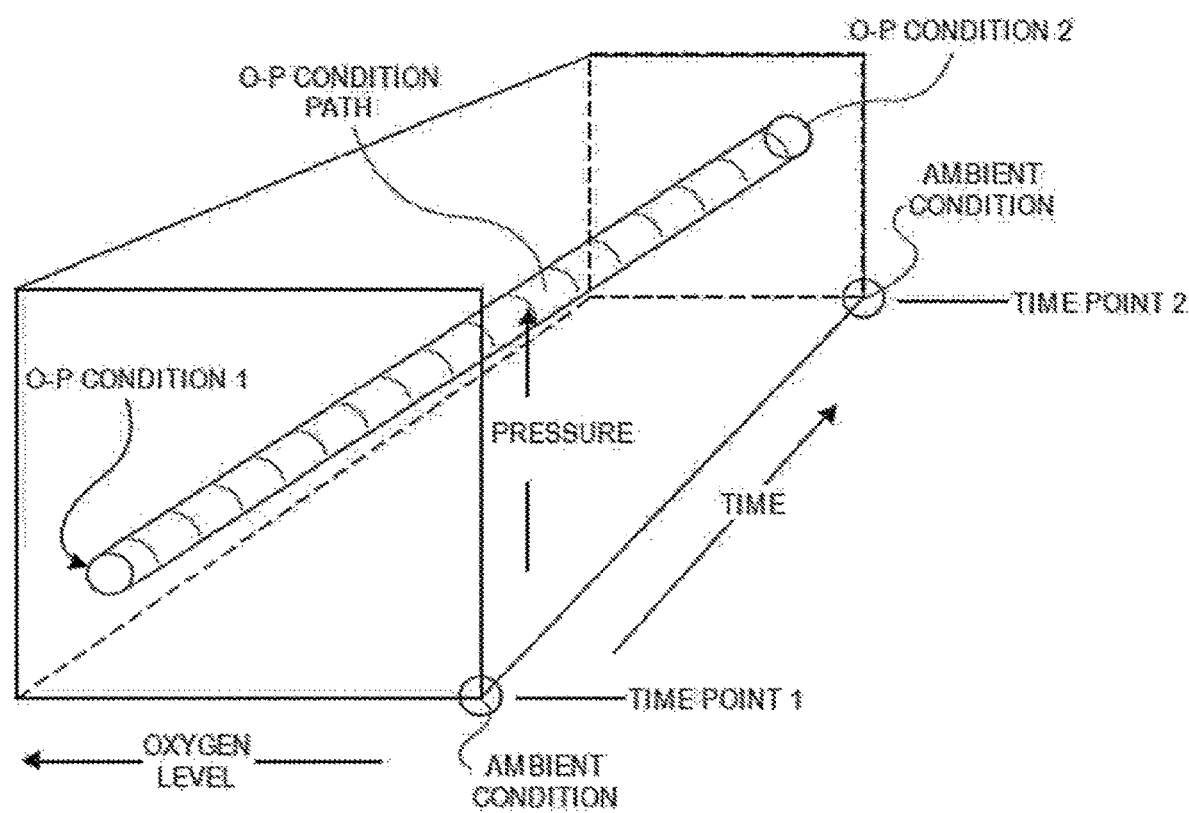
FIG. 1B is an X-Y-Z graphic representation of an oxygen level parameter (X-axis), a pressure level parameter (Y-axis), and time (Z-axis) for gaseous conditions in a cell culture incubator, with O-P Condition 1 shown at Time Point 1 and O-P Condition 2 shown at Time Point 2, having changed during the duration from Time Point 1 to Time Point 2.

FIGS. 1A and 1B

FIG. 1A shows a representation of two O-P conditions on a graph with X and Y-axes that intersect in the upper left corner of the graph, that intersection representing the ambient O-P condition. Oxygen concentration is represented on the X-axis, the oxygen concentrations used in embodiments of the technology are typically less than the ambient level. Total gas pressure is represented on the Y-axis, the total gas pressure concentrations used in embodiments of the technology are typically higher than the ambient total gas pressure. The ambient conditions for both oxygen level and total gas pressure, respectively, are located at the intersection of the X- and Y-axes, in the lower right corner of the graph.

Two exemplary O-P conditions are shown in FIG. 1: O-P condition 1 and O-P condition 2. Each O-P condition has an oxygen level less than the ambient level and a total pressure greater than the ambient lever. In comparing O-P condition 1 to O-P condition 2, it can be seen that O-P condition 1 has a lower level of oxygen and a lower total gas pressure, respectively, than the oxygen and total pressure values of O-P condition 2.

FIG. 1B shows another example of depicting two O-P conditions, showing them on a graph that includes the X- and Y-axes of FIG. 1, but also showing a Z axis representing time. The foreground X-Y axis at Time Point 1 shows O-P condition 1; the background X-Y axis at Time Point 2 shows O-P condition 2. In this example, by way of an O-P condition path, over the course of time between Time Point 1 and Time Point 2, the O-P condition has migrated from O-P condition 1 (having a relatively low oxygen level and a relatively low total gas pressure) to O-P condition 2, (having a relatively high oxygen level and a relatively high total gas pressure).

The O-P condition path, as shown in FIG. 1B, is schematically represented as a straight line, in which the oxygen level and the total gas pressure change in ramping manner, synchronously, and at the same relative rate. As described further below in detail, there are numerous variations of the nature of the O-P condition path. For example, the O-P condition path need not be a straight or direct ramping function, and the oxygen and total gas pressure conditions need not change synchronously or at the same relative rates.

Table 1: Gaseous Parameters

Table. 1 is a Table of variable atmospheric parameters that are regulated to varying degrees by embodiments of the technology.

TABLE 1

Variable Atmospheric Parameters

| Parameter | Parameter Terms | Regulation within an incubator, per embodiments of the present disclosure |
|---|---|---|
| Total Gas Pressure | pounds/square inch (PSI), as used herein, refers to lbs./square inch above ambient pressure (14.7 PSI). | Typically regulated at a level higher than ambient atmospheric pressure<br>Maintained by way of an air pumps and incubator chamber seals. Measured by pressure sensors. |
| Oxygen ($O_2$) Level | Concentration % or Partial Pressure | Typically regulated at a level lower than the ambient level of ~21% (or 160 mm Hg).<br>A low level of oxygen is maintained by addition of nitrogen (or carbon dioxide) to incubator chamber, thereby diluting the oxygen in the chamber.<br>In case of oxygen drifting to a level lower than desired, oxygen can be increased by influx of ambient air, bringing in oxygen at its ambient concentration.<br>Measured by oxygen sensors, data reported typically reported in concentration% terms. |
| Carbon Dioxide ($CO_2$) Level | Concentration % | Typically regulated at a level of 5%-10%, a level considerably above the ambient level of ~0.04%. The function of the carbon dioxide is to provide capacity for a bicarbonate-based buffering system in the cell culture medium.<br>Measured by carbon dioxide sensors, data reported typically reported in concentration % terms. |
| Nitrogen ($N_2$) Level | Concentration % | Typically maintained at a level that ranges near the ambient level of ~78% and upward toward 99%. The nitrogen level goes above ambient because it is used to displace oxygen to a low level.<br>Inflow of nitrogen is primarily regulated by the oxygen level, nitrogen serving as a diluter of oxygen. |
| Water Vapor | Concentration % | Water vapor can be maintained passively, by way of evaporation of standing water in the incubator, thus remaining at saturation level, or it may be maintained actively, at a level less than saturation. |
| Temperature | Degrees Celsius | Typically regulated at 37 degrees C., but may be regulated at a lower or higher level. |

Figure 2:
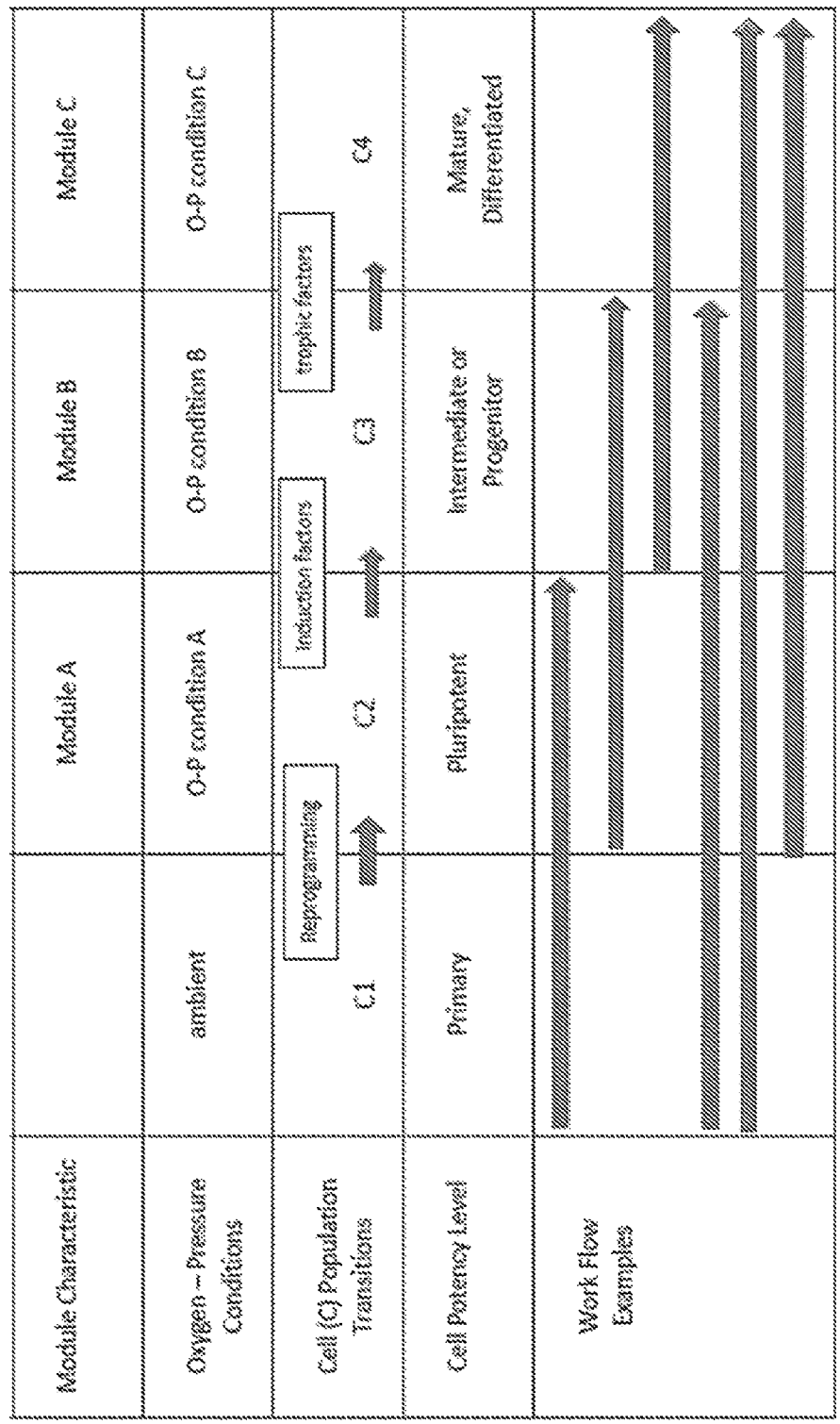
FIG. 2 is a schematic representation of the progression of a cell population through a series of modules that support the progression of the cell population toward a desired or targeted potency level phenotype, and stabilization at such phenotype.

FIG. 2 Potency-Level Phenotypic Modulation Through Various Workflows

FIG. 2 is a schematic representation of a progression of a cell population through various phenotypic manifestations (C1-C4) as directed by the cell culture conditions of a series of modules (Modules A, B, and C). "Modules", as used here, refers to a particular set of atmospheric conditions that is dictated and maintained by a controller that is operating a cell culture incubator. The conditions, according to these modules, support the progression of the cell population through phenotypic phases that move from a high potency level phenotype (on the left), such as being pluripotent, to a low potency level phenotype (on the right), such as a having mature and differentiated phenotype. Modules A-C refer to cell culture conditions that encourage a precursor cell phenotype to progress toward the "new" phenotypic state, and to stably maintain the cell population in that state. These culture conditions may include the composition of the cell culture medium, the presence of bioactive agents in the cell culture medium, as well as atmospheric conditions as provided by embodiments of the present technology described herein that relate to regulation of gaseous conditions such as oxygen level and total gas pressure (i.e., an "O-P condition").

The subject cell population of FIG. 2 begins its phenotypic progression within this scheme as a differentiated donor cell population C1, a primary cell population, from a donor subject. The primary cell population is in a differentiated state, although it may have a varying degree of amenability to being reprogramed to a high potency-level, depending to a significant extent on factors related to the specifics of the donor tissues, as, for example, the particulars of the site of the donor tissue or the age of the donor.

Starting with cell population C1, as described above, subsequent populations C2, C3, and C4, each with distinct phenotypic features, can be seen. Population C2, as it stabilizes in Module A, has an induced pluripotent stem cell phenotype, was derived from population C1. Population C3, in Module B, has an intermediately differentiated or differentiated cell progenitor phenotype, and is derived from population C2. Population C4, in Module C, has a mature, fully or substantially differentiated phenotype, and is derived from population C3.

By way of some specific examples, population C1 may be derived from a biopsy of a human being at any point in human development, including a neonate, an infant, a child, an adolescent, or an adult. From such a biopsy, fibroblast cells can grow out in culture. Population C1 can be driven to a yield population C2, an induced pluripotent stem cell (iPSC) cell population, by way of transfective reprogramming by Yamanaka factors (delivered, in some embodiments, by a self-replicating RNA vector) as well as by exposure to particular O-P conditions. The step of phenotypic progression from population C1 to C2 can be referred to as a reprogramming step.

Population C2 (an iPSC population) can then be driven to become an intermediately differentiated population C3, by way of exposure to various induction factors as well as to particular O-P conditions to become an intermediately differentiated population C3, as for example, a neural progenitor cell (NPC). The step of phenotypic progression from population C2 to C3 can be referred to as an induction step.

And finally, cell population C3, such as a neural progenitor cell, can be driven to assume a differentiated phenotype characteristic of cell population C4, such as that of a neuronal cell, or more particularly, a motor neuron cell, this progression being driven by exposure to various lineage-specific bioactive agents, such as growth factors, as well as exposure to particular O-P conditions. The step of phenotypic progression from population C3 to C4 can be referred to as a differentiation step.

Each of these steps is driven, at least in part, by an O-P condition, as described herein, a condition that includes both the oxygen level and the total gas pressure. The various O-P conditions that drive (1) a C1 potency level phenotypic population to a C2 potency level phenotypic population, (2) a C2 potency level phenotypic population to C3 phenotypic population, and (3) those that drive a C3 potency level phenotypic population to C4 potency level phenotypic population, respectively, may be variously similar to each or entirely different. The types of variation in O-P condition are described in detail elsewhere, herein.

As shown by directional arrows as the bottom of FIG. 3, units of cell culture workflow can be operated over any portion of an entire progression from a cell population C1 potency level phenotype to a C4 potency level phenotype. For example, a workflow may include any of the following sequences:

1. drive a cell population from a C1 potency level phenotype to a C2 potency level phenotype, per conditions of Module A.
2. drive a cell population from a C2 potency level phenotype to a C3 potency level phenotype, per conditions of Modules A and B.
3. drive a cell population from a C3 potency level phenotype to a C4 potency level phenotype, per conditions of Modules B and C.
4. drive a cell population from a C1 potency level phenotype to a C3 potency level phenotype, per conditions of Modules A and B.
5. drive a cell population from a C1 potency level phenotype to a C4 potency level phenotype, per conditions of Modules A-C.
6. drive a cell population from a C2 potency level phenotype to a C4 potency level phenotype per conditions of Modules A-C.

Table 2: Cell Populations, Potency Level Phenotypes, and Associated Markers

Table 2 provides a list of cell types, of varying potency level phenotypes and the cell culture modules that are included in the scope of the technology. These cells types are provided as exemplary cell types that are subject to methods of the technology; cell types responsive to these methods are not limited to this list.

The left column of Table 2 sets out rows dedicated to fibroblasts, mesenchymal stem cells, and hematopoietic cells. To the right of the left column are columns for Module A, Module B, and Module C, respectively. The modules, as described above, refer to the totality of cell culture conditions, including oxygen level and total gas pressure (the "O-P condition"). These O-P conditions encourage the phenotypic modulation of subject cell populations into potency level phenotypes, include a pluripotent phenotype (Module A), an intermediate potency level or progenitor cell phenotype (Module B), or a mature and differentiated cell phenotype (Module C). Markers (or biomarkers) that identify various cell types are shown within parentheses following the various cell phenotype types.

TABLE 2

Cell Populations: Modulation of Potency Level Phenotype and Biomarkers

| source population: mature, differentiated | Module A pluripotent derivative | Module B intermediate potency progenitor cell | Module C mature differentiated cell |
|---|---|---|---|
| Skin biopsy to obtain fibroblasts, human donors | Induced pluripotent stem cell (iPSC) derived by transfection with transcription factors and exposure to O-P conditions A | Derived by exposure to induction factors and to O-P conditions B<br>A. Neural progenitor cells (NPS)<br>B. Cardiomyocytes (SIRPA, cTNT, NKX2.5)<br>C. Pancreatic progenitors (GP2, FXYD2, PDX-1)<br>D. Liver progenitor (CPM, CD133, GATA2)<br>E. Retinal Epithelium progenitors<br>F. Pre-adipocytes (CD44, CD90, CD105, CD24, ZFP423)<br>G. Endothelial progenitors (CD44, CD90, CD105, CD24, ZFP423) | Derived from progenitor cells and exposure to trophic factors and to O-P conditions C<br>A1. Motor neurons<br>A2. Neuronal<br>B. Mature cardiac cells<br>C. Pancreatic beta-cells (GLUT2, IGFR, IR)<br>D. Mature liver cells (CK18, ALB, Glycogen)<br>E. Retinal cells<br>F. Adipocytes (Asc-1, PAT2, Adiponectin, Adipoq, and ALK7)<br>G. Endothelial Cells |
| Mesenchymal stem cells (MSCs) (CD44+, CD73+, CD90+, CD45−, CD34−) | Osteochondreal progenitor | Osteoblast (osteocalcin, DMP-1, osteoahderin) | Osteocyte (SOST, DMP1, FGF23)<br>Chondrocyte (SOX9, COL2A1) |
| iPSC-derived or primary hematopoietic cells | Hematopoietic Stem Cells (CD34 +, CD38−, CD90+, CD45RA−) | Lymphoid progenitor (CD34, CD43, Flt-3/Flk-2, IL-7 R alpha/CD127, Neprilysin/CD10) | Immune Cells:<br>T cell (CD3),<br>B cell (CD19, CD20),<br>NK cell (CD16, CD56) |

TABLE 3

Terminology

| Term | Explanation and Relevance |
|---|---|
| BM iPSC-NSC | Neural stem cells ("NSC") generated from bone marrow-derived induced pluripotent stem cells ("BM iPSC"). |
| CB iPSC-NSC | Neural stem cells ("NSC") generated from cord blood-derived induced pluripotent stem cells ("CB iPSC"). |
| CD34 | CD34 Molecule: A marker for early hematopoietic stem cells. |
| CD34+CD43medCD45+ | A distinct population of hematopoietic progenitor cells. |
| CD43 | Sialophorin: A marker for early hematopoietic stem cells. |
| CD45 | Protein tyrosine phosphatase, receptor type C: Marker used to distinguish the early lymphocyte progenitor cell lineage. |
| CD57 | B3GAT1 (beta-1,3-glucuronyltransferase 1): A marker for primed state pluripotency in stem cells. |
| ChAT | Choline acetyltransferase: A neurotransmitter protein that is highly abundant in motor neurons. |
| FDR | False discovery rate: the Benjamini-Hochberg procedure is used. |
| GO term | Gene ontology term: Biological function classification of a group of gene products (protein, non-coding RNA, or macromolecular complex) based on the literature. |
| iPSC | Induced pluripotent stem cell |
| LIF | Leukemia inhibitory factor |
| MAP2 | Microtubule associated protein 2: A marker for mature neurons. |
| MFI | Mean fluorescence intensity: the geometric mean fluorescence intensity is extracted from flow cytometry data. |
| NANOG | Nanog homeobox: A gene important for maintenance of pluripotency. |
| NOGGIN | A protein important for neural patterning; used to derive neural stem/progenitor cells from iPSCs. |
| NES | Nestin: A marker commonly used to identify neural stem/progenitor cells. |
| NSC | Neural stem cell: A multipotent progenitor cell that can give rise to multiple neuronal lineages. |

TABLE 3-continued

Terminology

| Term | Explanation and Relevance |
|---|---|
| PAX6 | Paired Box 6: A marker commonly used to identify neural stem/progenitor cells. |
| POU5F1 | POU Class 5 homeobox: The human homolog of mouse OCT4 gene; important for maintenance of pluripotency. |
| psa-NCAM | Polysialic acid neural cell adhesion molecule: A marker used to identify neural stem/progenitor cells. |
| SMI-32 | Antibody clone targeting the neurofilament-H gene; used to identify motor neurons. |
| SOX2 | SRY-Box 2: A gene important for maintenance of pluripotency. |
| SYN1 | Synapsin 1: A marker for mature neurons. |
| whole-transcriptome mRNA-seq | A method to sequence fragments of all messenger RNAs present within a population of cells. |

Neural Cell Differentiation from iPSC's

Data are reported and depicted (FIGS. 3A-6B) here showing that human iPSCs that are cultured under elevated atmospheric pressure and hypoxic conditions have altered epigenetic and metabolic gene expression profiles that reflect a promotion of differentiation and maturation of neurons.

The biological effects of physical forces on stem cell maintenance and differentiation is becoming better understood as the number of studies demonstrating the positive influence various forms of physical force have on stem cell differentiation. Traditional methods of stem cell culture generally have not systematically varied the physical forces that exist in vivo, such as three-dimensional cell-to-cell interactions and variations in oxygen level and atmospheric pressure in various tissues and compartments of the human body. Physiologically-relevant oxygen gas concentration and three-dimensional culture in the form of organoid models have been used in the study of stem cell differentiation, yet consideration of atmospheric pressure has not been evaluated in this context.

The role of atmospheric pressure and hypoxic conditions on stem cell state over time in culture in human donor iPSC lines is reported here; aspects of the data are provided in FIGS. 3A-6B. Three different human donor iPSC lines were cultured under atmospheric variables included 5% or 15% oxygen, each in combination with either ambient atmospheric pressure (+0 PSI) or elevated atmospheric pressure (+2 PSI). Thus, experimental groups included (1) 5% oxygen at +0 PSI, (2) 5% oxygen at +2 PSI, (3) 15% oxygen at +0 PSI, and (4) 15% oxygen at +2 PSI.

Cultures were examined for global gene expression changes by mRNA-seq and immunofluorescence staining for pluripotency and differentiation markers over time. iPSCs cultured under elevated atmospheric pressure (+2 PSI) and 15% oxygen for 7 passages (unlike their cohort cultures exposed to ambient atmospheric pressure or iPSCs cultured in 5% oxygen) show morphological and global gene expression changes that are consistent with a primed or differentiated state. As early as passage 3, iPSCs cultured under elevated atmospheric pressure and 15% oxygen exhibit a shift in metabolic gene expression profile and an up-regulation of genes involved in epigenetic regulation. To examine the combined influence of elevated pressure and protein and/or small molecule factors in the medium, directed-differentiation was performed of both (1) iPSCs into neural progenitors and (2) neural stem cells (NSCs) into motor- and CNS-type neurons, and show that 5% oxygen and elevated pressure (+2 PSI) increased the level of expression of neural progenitor and neuronal maturation markers, respectively. These observations suggest that atmospheric pressure (in conjunction with a hypoxic oxygen level) during culture can be a significant regulator of stem cell differentiation. Manipulation of these atmospheric variables can be leveraged towards encouraging the maturation of stem cells toward neurons that are suitable for translational studies in vitro and in the clinic.

Figure 3A:
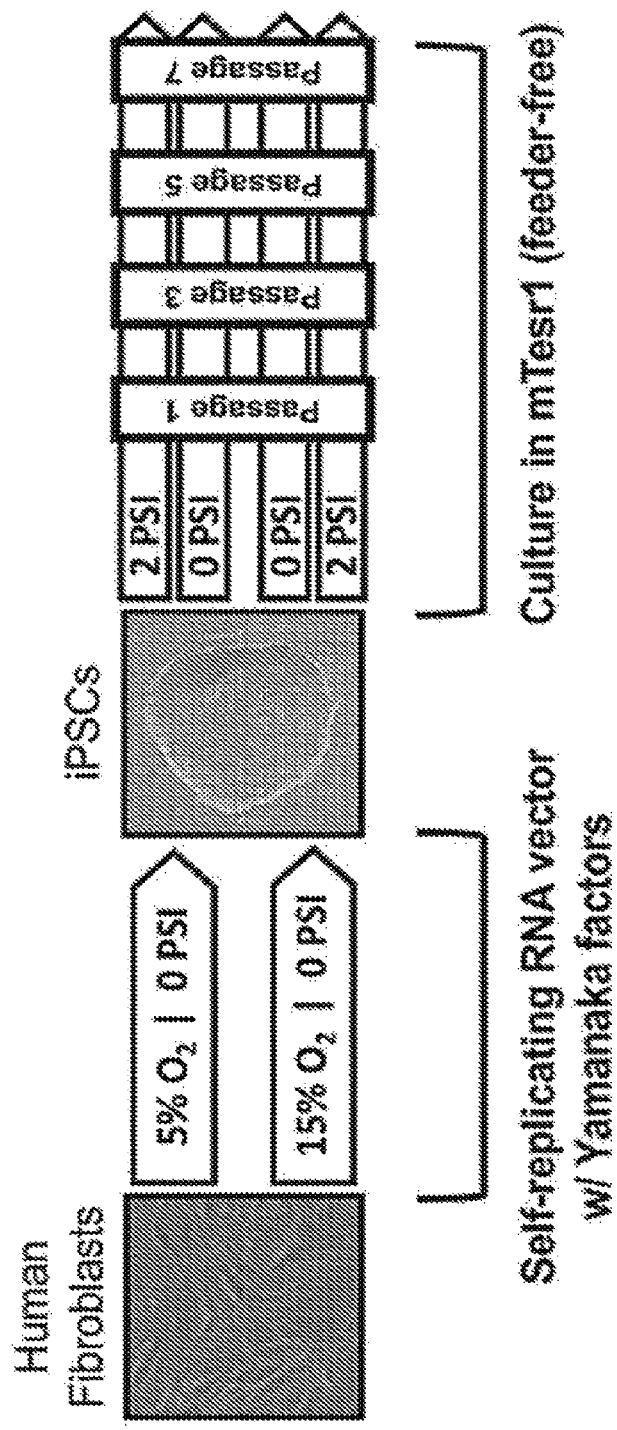
FIGS. 3A-3H show data from long-term culture of induced pluripotent stem cells (iPSCs) in 15% oxygen and increased atmospheric pressure, which induces nuclear PAX6 expression and promotes differentiation. Data reported in all figures, unless otherwise specified, are derived from studies of cells cultured in the Avatar™ incubator (Xcell Biosciences, San Francisco, Calif.), which is able to control total atmospheric pressure to hyperbaric levels, and oxygen level to hypoxic levels.

FIG. 3A is a schematic diagram of the experimental design. Two human fibroblast cell lines and one human CD34+ cord blood cell line were re-programmed using a self-replicating RNA vector (ReproRNA, Stemcell technologies) containing the transcription factors OCT4, KLF-4, SOX2, GLIS1, and c-MYC or episomal vector (National Institutes of Health, NIH) expressing re-programming factors, respectively to create induced pluripotent stem cells (iPSC). The two fibroblast lines were purchased from the Coriell Institute and re-programmed in the indicated oxygen and atmospheric pressure conditions and clonal lines established. The CD34+ cord blood iPSC line was obtained from the NIH Health. Each iPSC line was then cultured in feeder-free conditions in mTesr1 medium in the indicated oxygen and atmospheric pressure conditions in parallel, and analyzed by flow cytometry and immunofluorescence microscopy or mRNA-seq (passage 3 and 7) for protein and gene expression changes, respectively.

Figure 3B:
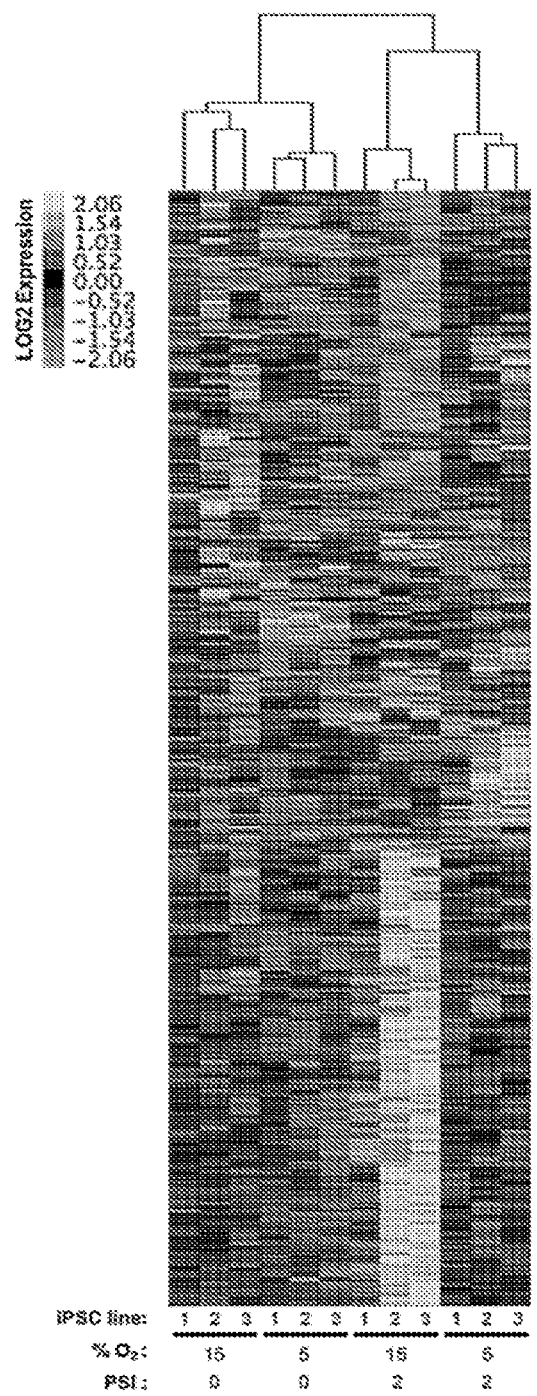

FIG. 3B shows an unsupervised hierarchical clustering of cumulative differentially expressed genes (763 total) by whole-transcriptome RNA-seq at passage 7 in the indicated $O_2$ and PSI values. This figure shows that long-term culture of iPSC lines in elevated atmospheric pressure leads to significant differentially expressed genes constituting roughly 3% of all known coding genes in the human genome, indicating that there is a large influence of elevated atmospheric pressure on the iPSC transcriptome. The columns representing 15% $O_2$+2 PSI indicate large clusters of genes that are higher in expression (these are yellow in the original micrograph) or lower in expression (these are blue in the original micrograph) after normalization to median log base 2 gene expression across all samples for each gene (rows). A minor cluster of genes that are higher in expression specifically in 5% O2+2 PSI samples is also observed, indicating a unique set of genes that are positively regulated in this combination of oxygen concentration and pressure.

Figure 3C:
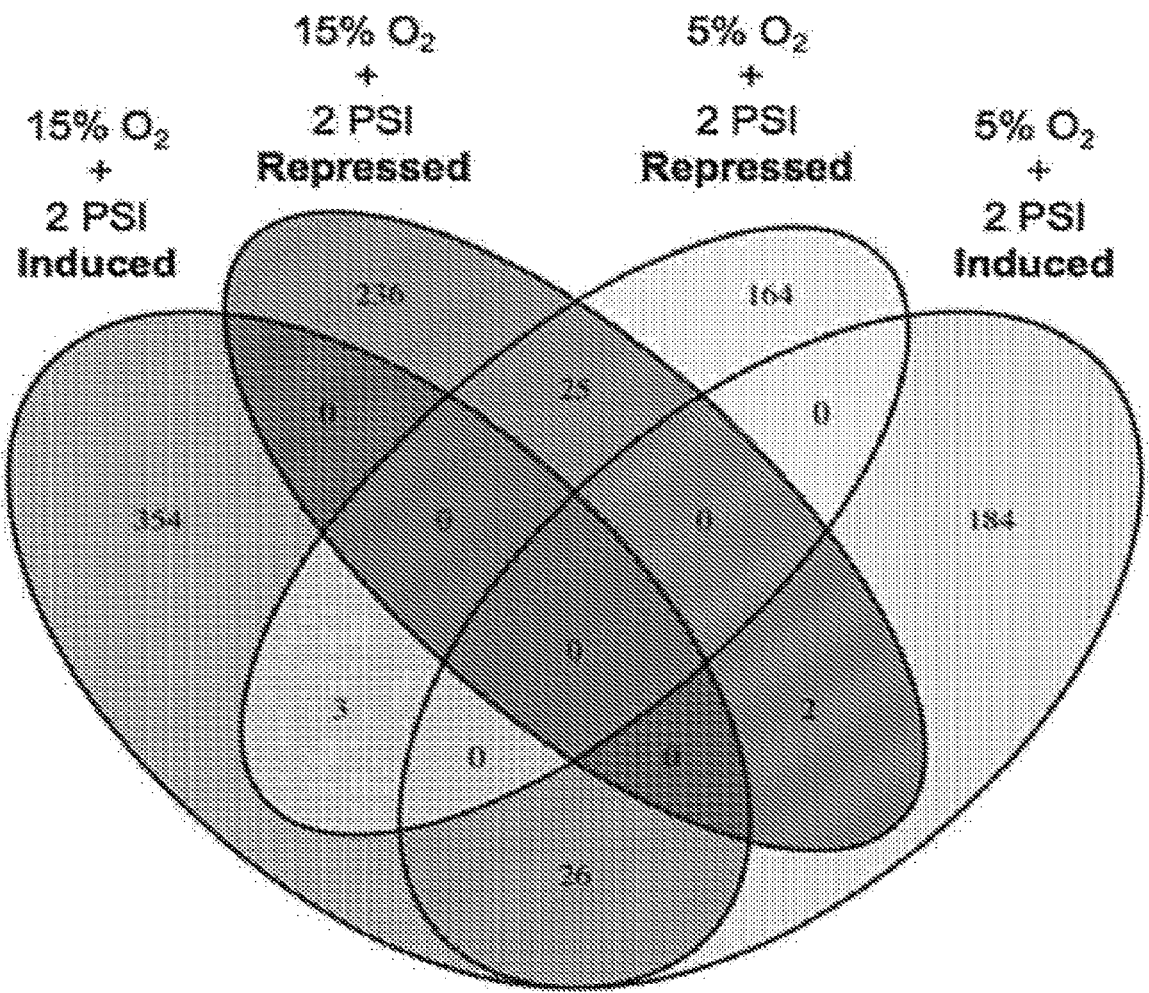

FIG. 3C is a Venn diagram that shows significant differentially expressed genes (as shown in FIG. 3B) showing overlap between analysis groups. The numbers in each Venn diagram compartment represent significantly differentially expressed genes between 15% O2+2 PSI vs. 15% O2+0 PSI and 5% O2+2 PSI vs. 5% O2+0 PSI, and the overlap of common differentially expressed genes between each analysis group. The larger number of differentially expressed genes in the 15% $O_2$ analysis group indicates that elevated atmospheric pressure functions synergistically with higher oxygen to influence gene expression changes in iPSCs. The disparity in the total number of differentially expressed genes displayed in this figure compared to FIG. 3B is due to the fact that no genes were filtered based on differential expression between 15% $O_2$ vs 5% $O_2$, in contrast to FIG. 3B.

Figure 3D:
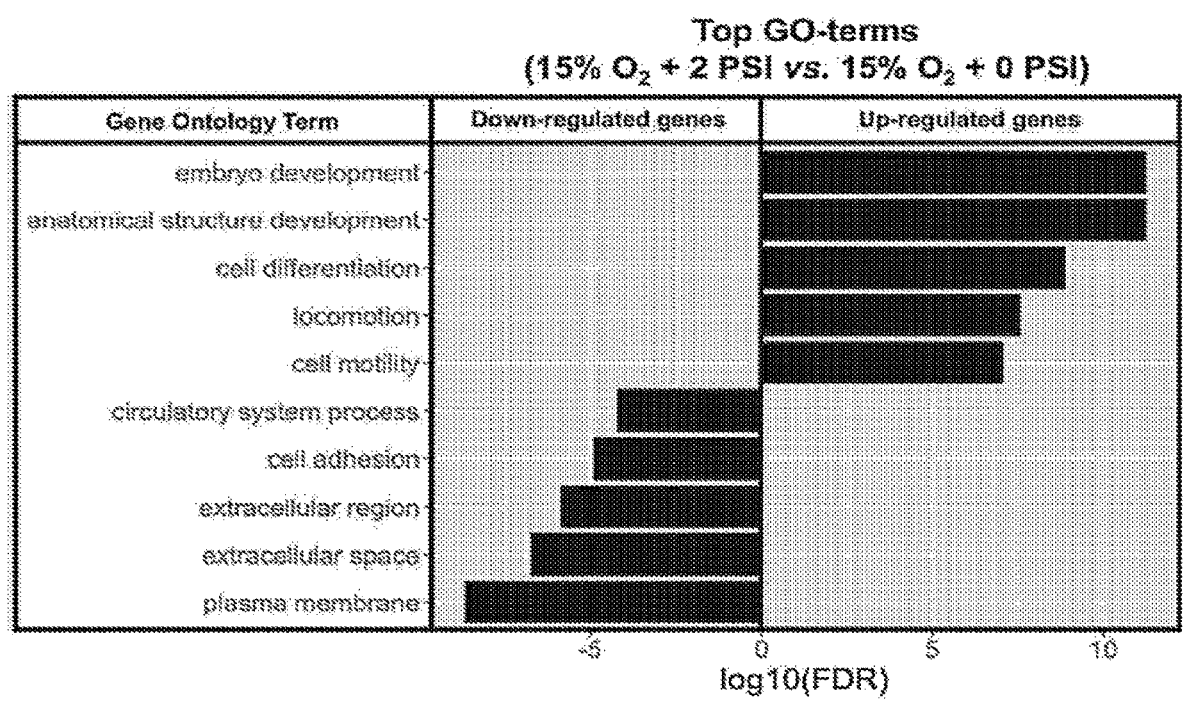

FIG. 3D shows the top five gene ontology (GO) terms for both up-regulated and down-regulated differentially expressed genes between 15% O2+2 PSI vs. 15% O2+0 PSI in iPSCs cultured to passage 7. Gene ontology enrichment is ranked according to adjusted p-value of the false discovery rate (FDR) and displayed on log 10 scale. The number of significant differentially expressed genes for each GO term is displayed in the bar graph. The top gene ontology pathways that are enriched in 15% O2+2 PSI vs. 15% O2+0 PSI differential gene expression analysis relate to morphogenesis of cells, indicating that 15% $O_2$ and elevated atmospheric pressure is influencing gene regulatory pathways that govern a phenotypic change in iPSCs. These results suggest that elevated atmospheric pressure (at 15% $O_2$) influences the morphology and differentiation state of the cell population at this time-point (passage 7) at the level of transcription.

Figure 3E:
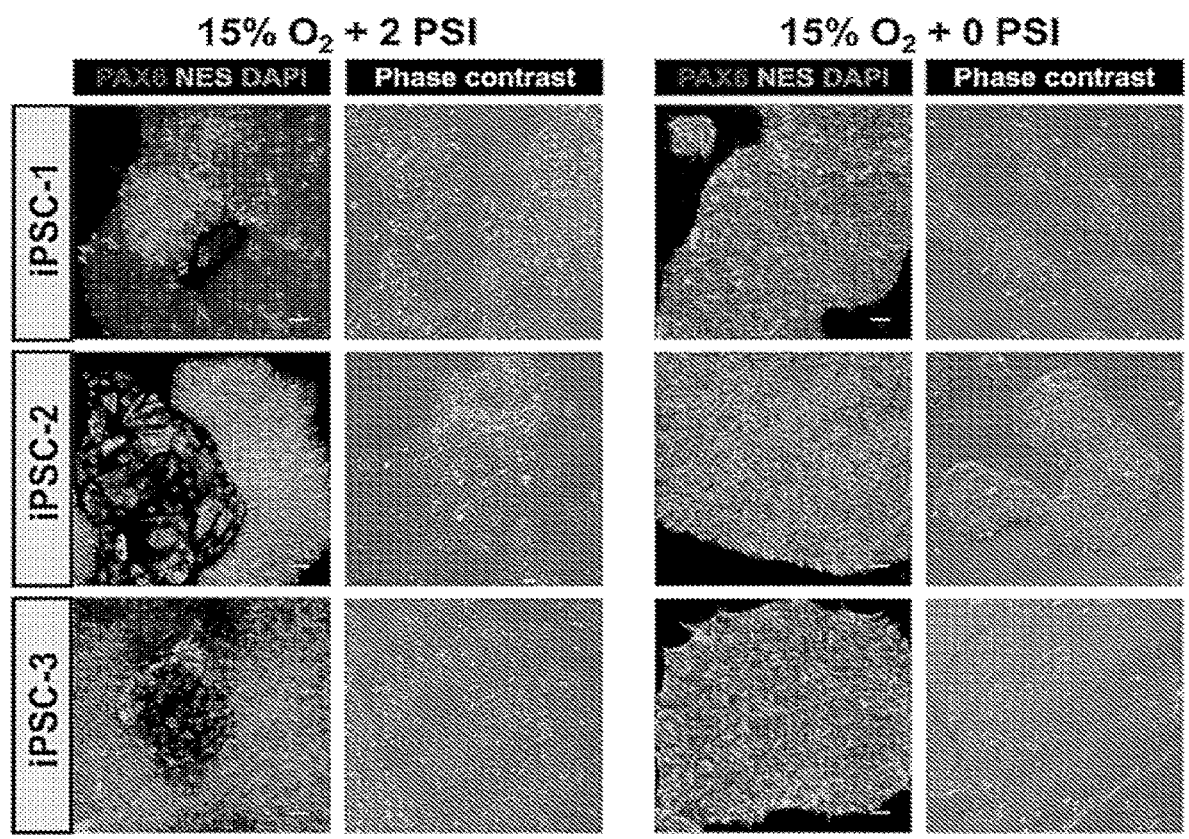

FIG. 3E shows representative immunofluorescence and phase contrast images of passage 7 iPSCs showing expression of markers PAX6 and NES in the indicated culture conditions. Two proteins that are highly expressed in primitive ectoderm, PAX6 and NES, are labelled by immunofluorescence staining and visualized at passage 7, with observable nuclear PAX6 expression specifically in iPSCs cultured at 15% O2+2 PSI. NES staining, although present in iPSCs cultured at ambient atmospheric pressure, has a unique cytoplasmic localization pattern in 15% O2+2 PSI in iPSC lines 2 and 3, but not as pronounced in line 1. Examination of the morphology of the iPSCs cultured in 15% O2+2 PSI by phase contrast indicates a flattened cell-body appearance with an increased cytoplasm-to-nucleus ratio relative to their counterparts in ambient atmospheric pressure, which is indicative of cellular differentiation. Taken together, these results suggest that iPSCs cultured in 15% O2+2 PSI at passage 7 may be differentiated towards a state indicative of primitive ectoderm.

Figure 3F:
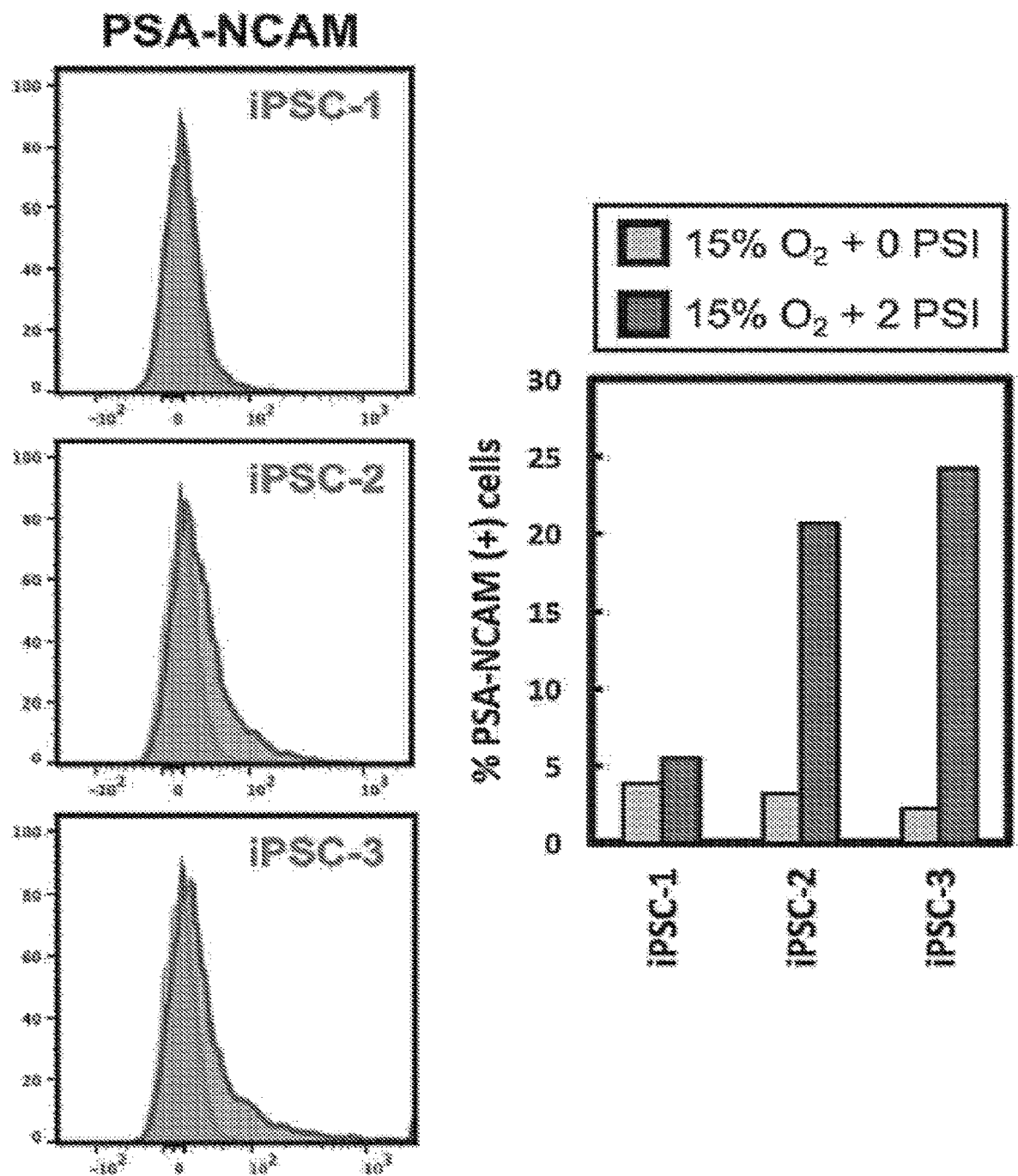
Figure 3G:
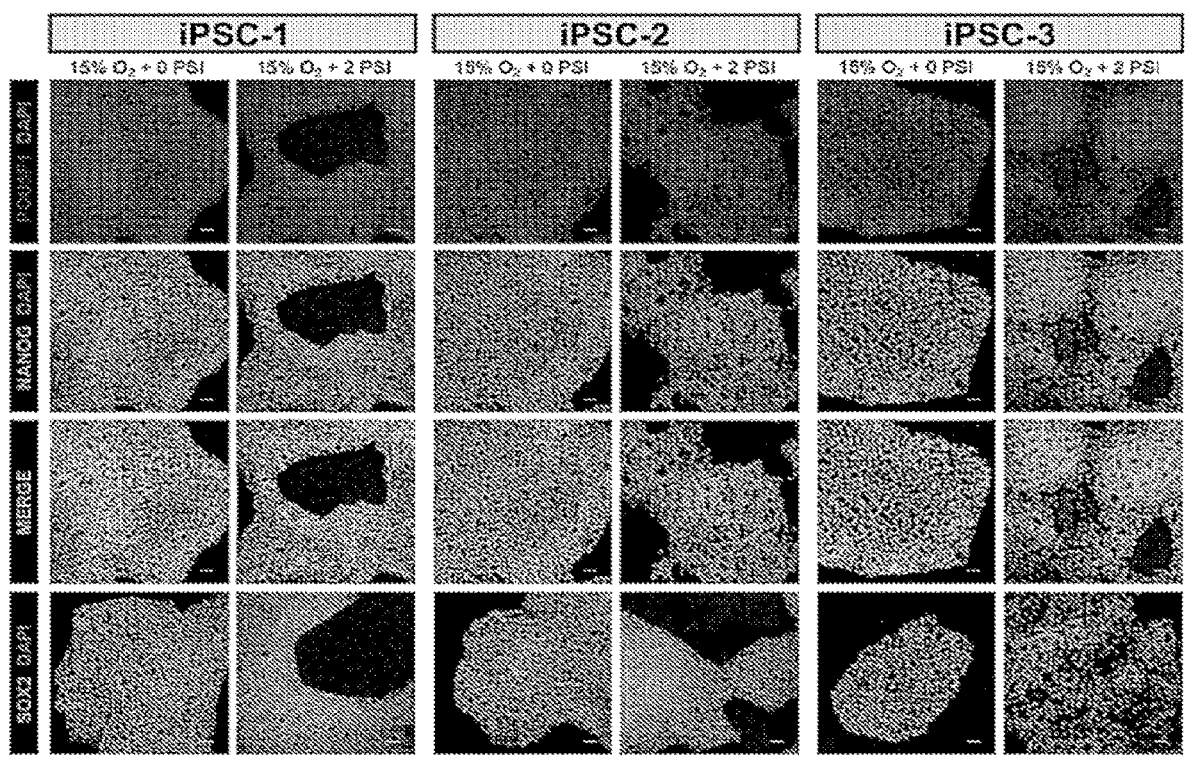

FIG. 3F shows flow cytometry data of psa-NCAM stained iPSCs at passage 7 cultured in 15% O2+0 PSI (light histogram) and 15% O2+2 PSI (dark histogram). The summary of the % psa-NCAM positive (+) cells is shown in the column graph on the right. Gating of psa-NCAM positive cells was performed using un-stained iPSCs. psa-NCAM, the polysialylated isoform of neural cell adhesion molecule (NCAM), is a cell surface glycoprotein that regulates cell-to-cell interactions and is first expressed in the early neural ectoderm cell lineage during embryonic development, or during in vitro stem cell differentiation to neural ectoderm. The presence of psa-NCAM in iPSC lines 2 and 3 at passage 7 indicate that these cell populations contain individual cells that are differentiated down the neural ectoderm lineage, whereas line 1 has not yet committed to this lineage. The absence or delayed expression of psa-NCAM in line may be due to epigenetic differences that infer some resistance to differentiation FIG. 3G shows representative immunofluorescence images of passage 7 iPSCs showing expression of markers POU5F1, NANOG, and SOX2 in the indicated culture conditions. The expression of pluripotency markers POU5F1, NANOG, and SOX2 is largely retained in iPSCs cultured in 15% O2+2 PSI, suggesting that these cells have not fully exited the pluripotent state, with the exception of sporadic cells stained negative within each population.

Figure 3H:
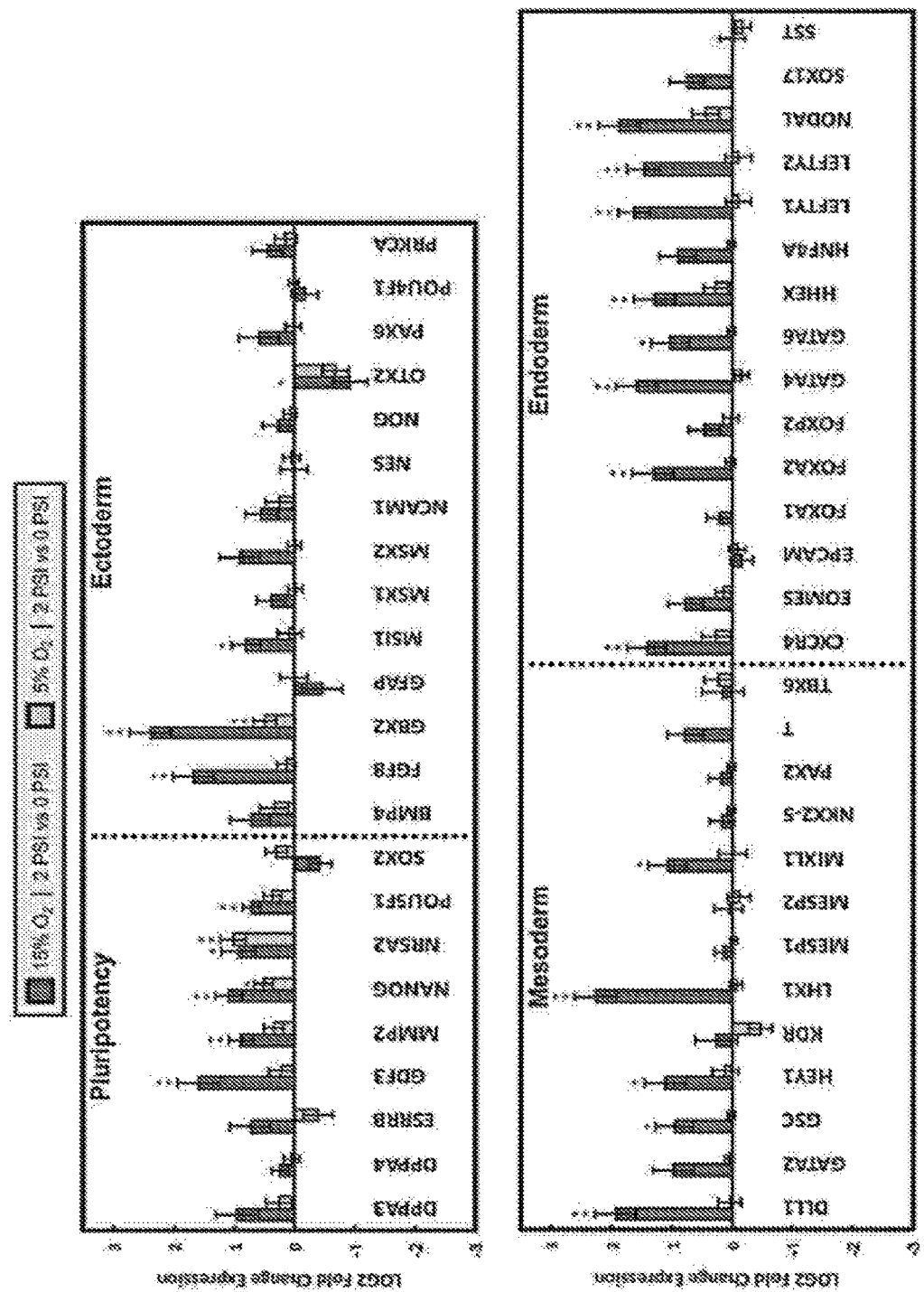

FIG. 3H shows pluripotency and germ layer differentiation marker gene expression from DEseq2 log 2 fold changes between both 15% O2+2 PSI vs. 15% O2+0 PSI (blue bars) and 5% O2+2 PSI vs. 5% O2+0 PSI (red bars) iPSC lines. The increased expression of germ layer commitment markers for ectoderm, mesoderm, and endoderm in iPSCs cultured in 15% $O_2$ and elevated atmospheric pressure are indicative of cellular priming for differentiation, as upregulation of these genes is observed during the transition from naïve to primed state pluripotency in both embryonic and induced pluripotent stem cells. Upregulation of these germ layer commitment markers is also indicative of an intermediary differentiation step in which iPSCs are transitioning from the pluripotent state to any one or more germ layers.

Figure 4A:
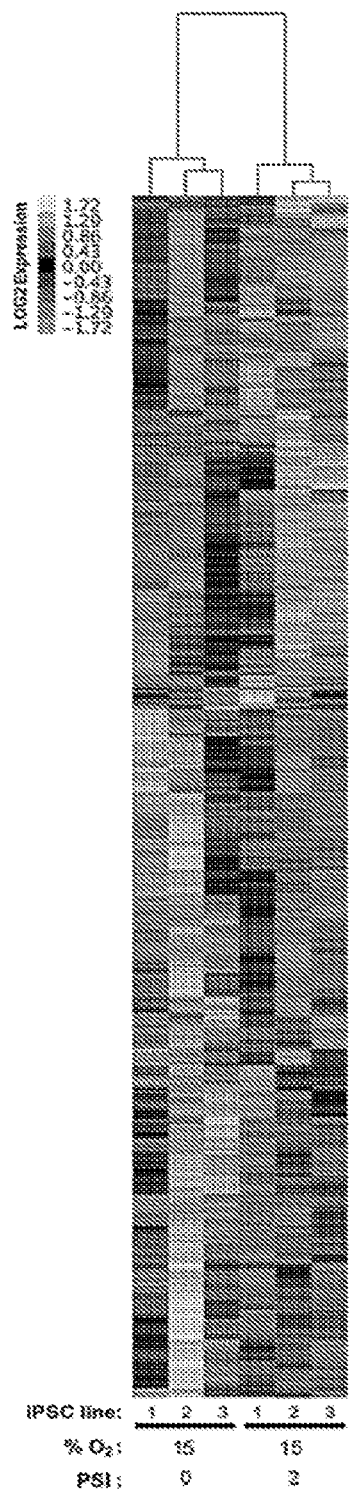
FIGS. 4A-4F show data reflecting a shift in metabolic and epigenetic gene signature observed in iPSCs cultured short-term in high oxygen and increased atmospheric pressure.

FIGS. 4A-4F show data reflecting a shift in metabolic and epigenetic gene signature observed in iPSCs cultured short-term in high oxygen and increased atmospheric pressure. FIG. 4A shows unsupervised hierarchical clustering of differentially expressed genes (1473 total) by whole-transcriptome RNA-seq at passage 3 with adjusted FDR between 15% O2+2 PSI vs. 15% O2+0 PSI using DEseq2. n=3 independent donor iPSC lines, two from human fibroblast (iPSC lines 1 and 2) and one from human CD34+ cord blood (iPSC line 3) cells. This figure demonstrates how short-term culture of iPSC lines in 15% $O_2$ and elevated atmospheric pressure leads to significant differentially expressed genes constituting roughly 5.9% of all known coding genes in the human genome, showing that there is a large influence of elevated atmospheric pressure on the iPSC transcriptome.

Figure 4B:
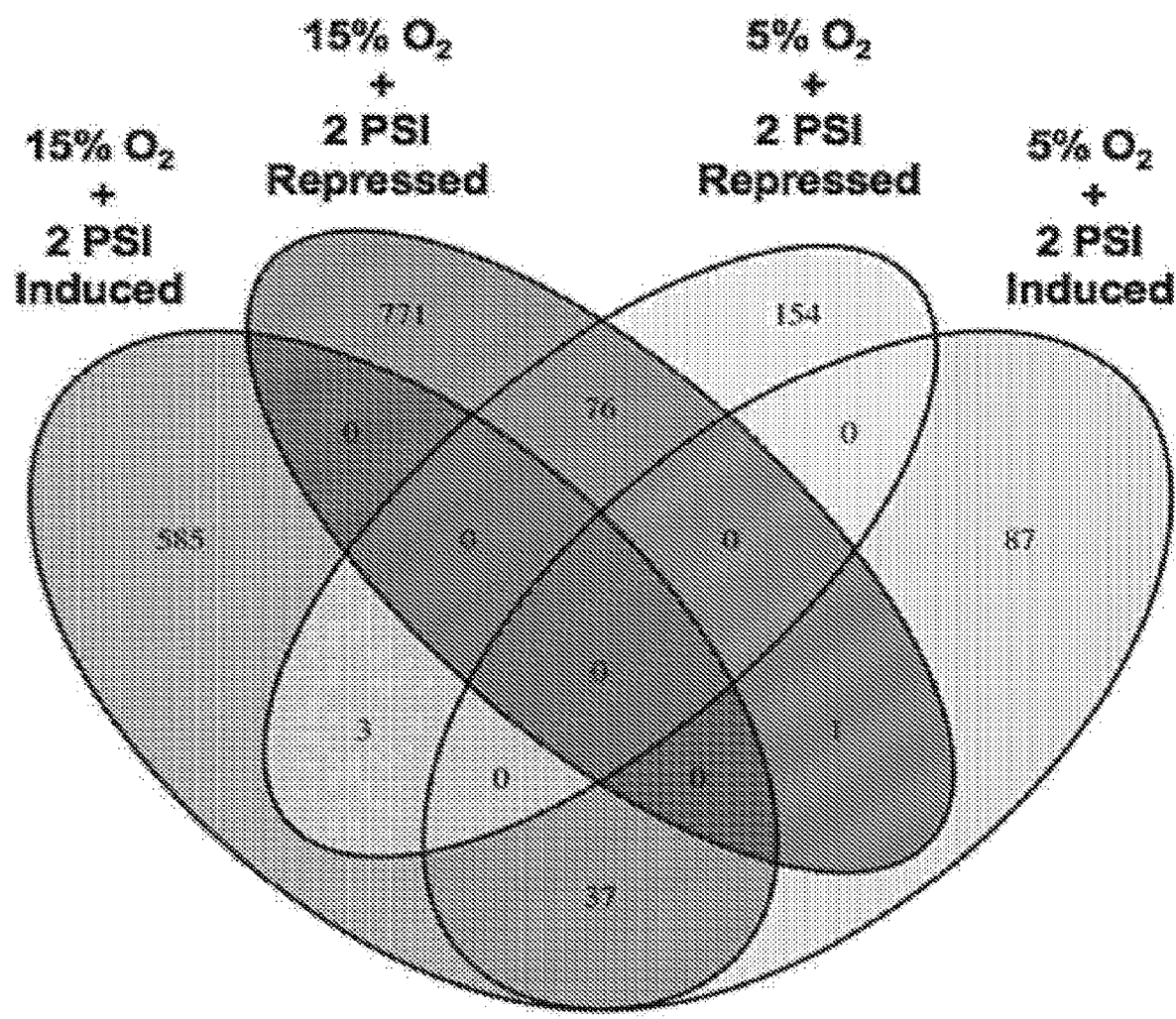

FIG. 4B is a Venn diagram of showing significant differentially expressed genes from (FIG. 1A) and additionally, differentially expressed genes between 5% O2+0 PSI vs. 5% O2+2 PSI. The numbers in each Venn diagram compartment represent significantly differentially expressed genes between 15% O2+2 PSI vs. 15% O2+0 PSI and 5% O2+2 PSI vs. 5% O2+0 PSI, and the overlap of common differentially expressed genes between each analysis group. The larger number of differentially expressed genes in the 15% $O_2$ analysis group indicates that elevated atmospheric pressure functions synergistically with higher oxygen to influence gene expression changes in iPSCs.

Figure 4C:
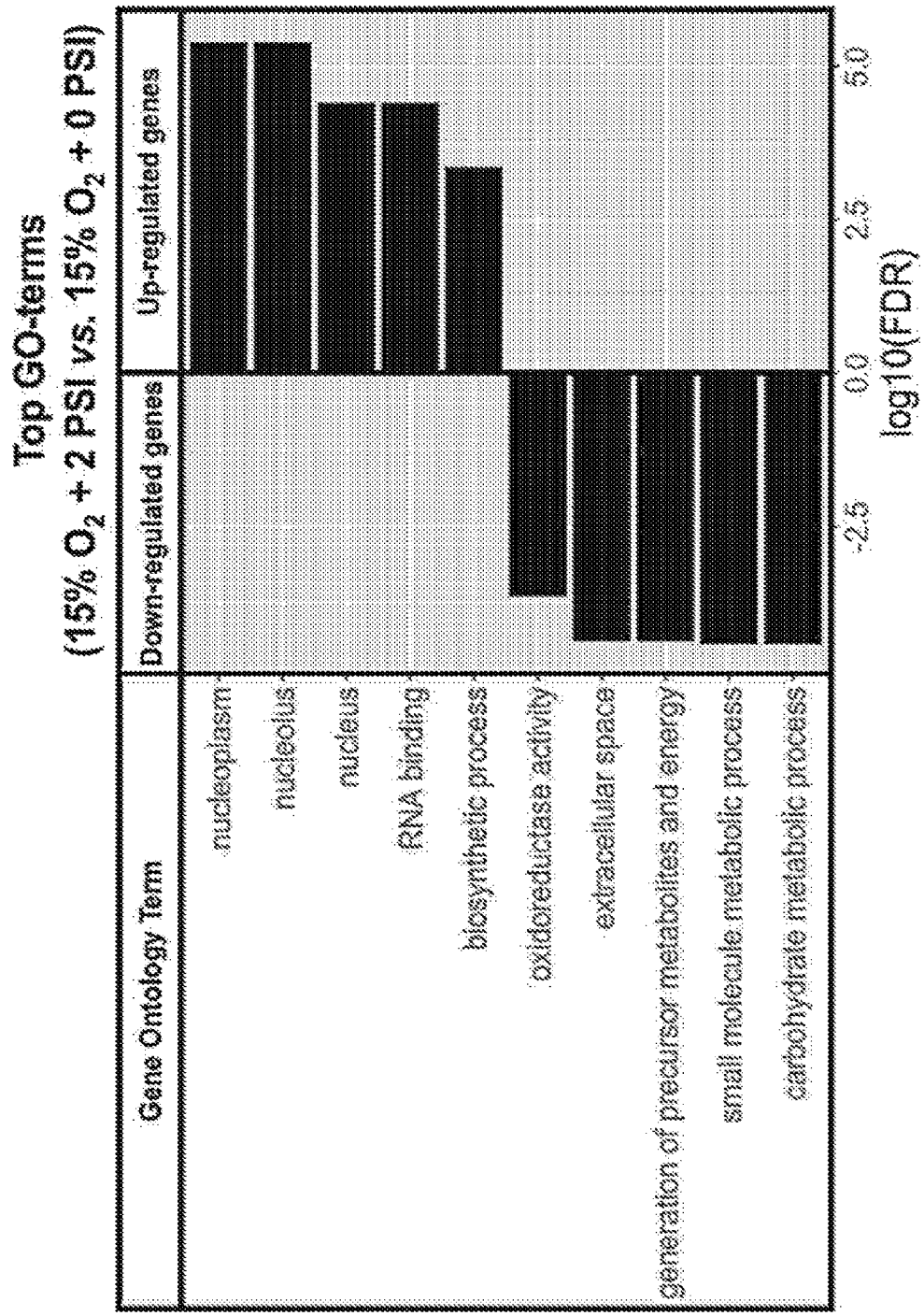

FIG. 4C shows the top five GO (gene ontology) terms for both up-regulated and down-regulated differentially expressed genes between 15% O2+2 PSI vs. 15% O2+0 PSI. Gene ontology enrichment ranked according to adjusted p value (FDR) and displayed on log 10 scale. The number of significant differentially expressed genes for each GO term is displayed in the bar graph.

The top (gene ontology) pathways that are enriched in 15% O2+2 PSI vs. 15% O2+0 PSI differential gene expression analysis (nucleoplasm, nucleolus, nucleus, RNA binding, and biosynthetic process) relate to both cellular metabolism and regulation within the cell nucleus. These results suggest that elevated atmospheric pressure (at 15% $O_2$) influences cellular functions relating to metabolism and gene regulation within the nuclear compartment at passage 3 within this population of cells. The significance of these findings is that enrichment for these gene ontology pathways may be indicative of the phenotypic changes observed in long-term culture of iPSCs in 15% O2+2 PSI, at passage 7.

Figure 4D:
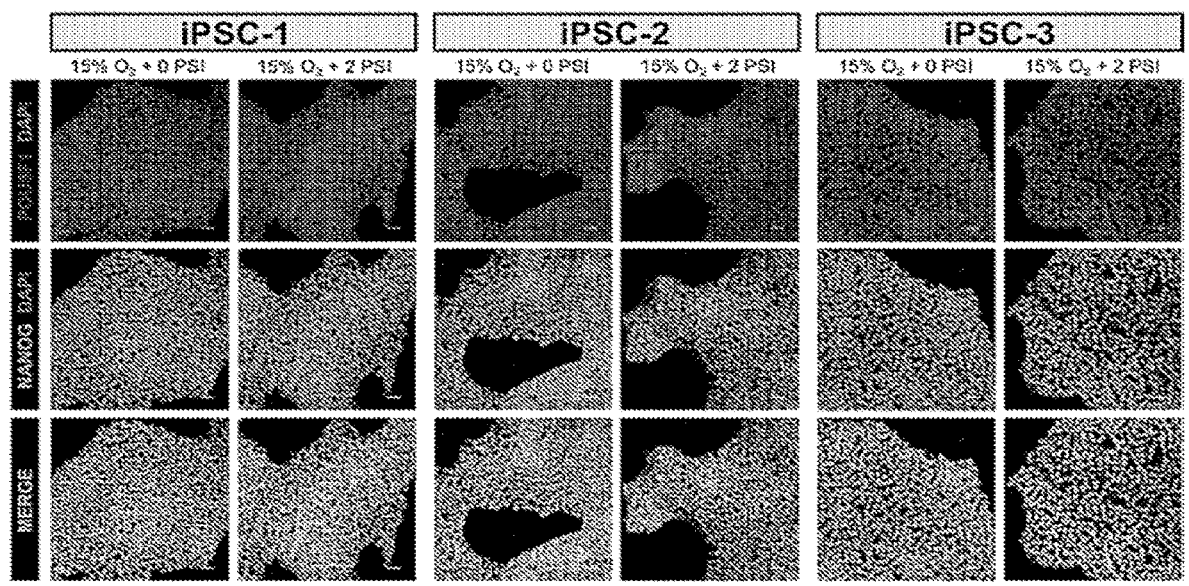

FIG. 4D shows representative immunofluorescence images of passage 3 iPSCs showing expression of POU5F1 and NANOG in the indicated culture conditions. The expression of pluripotency markers POU5F1 and NANOG is retained in iPSCs cultured in 15% O2+2 PSI, suggesting that these cells have not exited the pluripotent state up to passage 3 in culture.

Figure 4E:
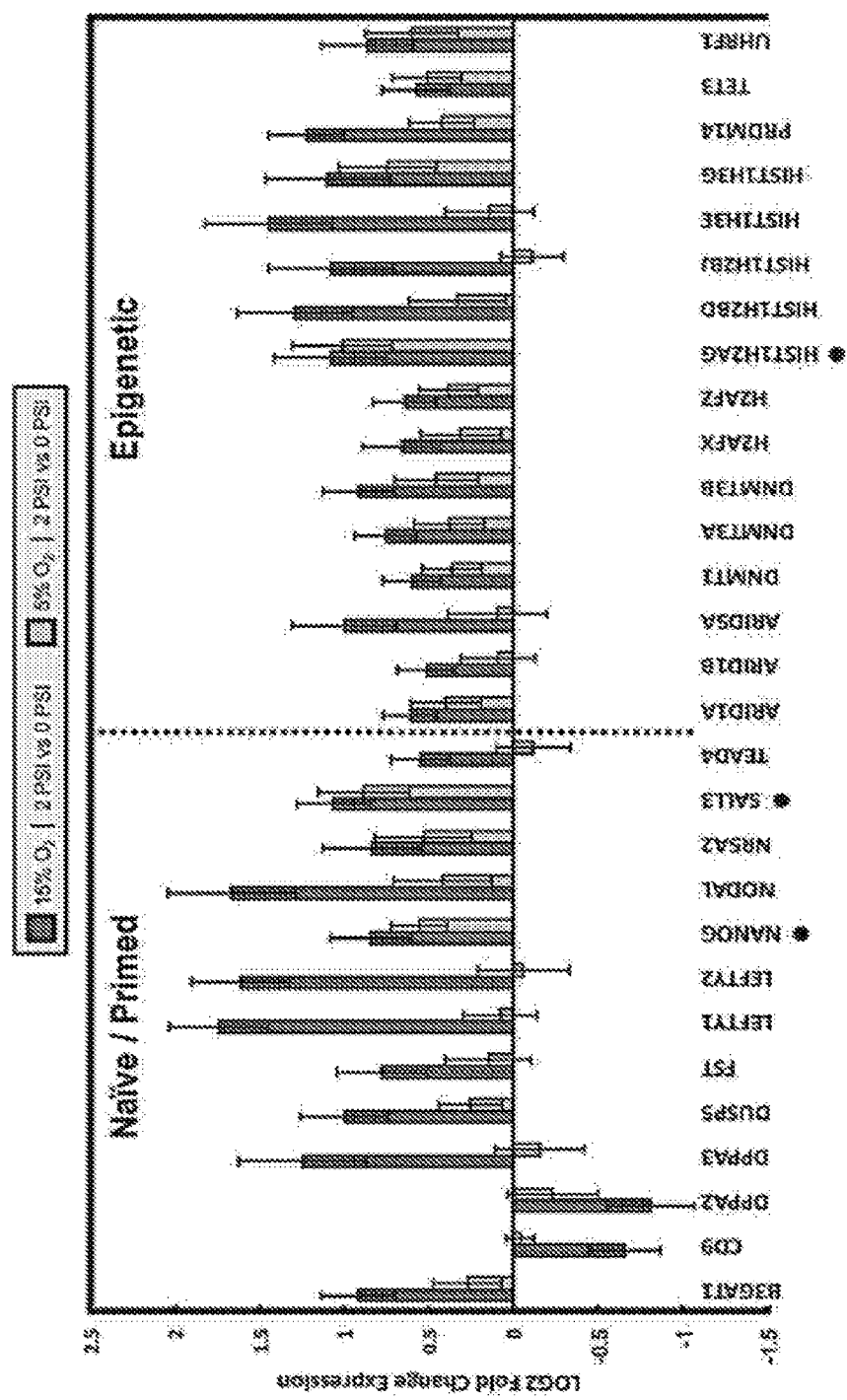

FIG. 4E shows naïve/Primed associated genes and epigenetic regulator gene expression from DEseq2 log 2 fold changes between both 15% O2+2 PSI vs. 15% O2+0 PSI (dark bars) and 5% O2+2 PSI vs. 5% O2+0 PSI (light bars) iPSC lines. All 15% O2+2 PSI vs. 15% O2+0 PSI (blue bars) have adjusted p-value (FDR)<0.05, and those gene names with a black dot are also significant for 5% O2+2 PSI vs. 5% O2+0 PSI (red bars). The increased expression of genes coding for epigenetic regulators in 15% O2+2 PSI at passage 3 could in part explain the differentiation phenotype observed at passage 7, as it is known that progressive methylation of the genome is characteristic of transition from pluripotent stem cells to differentiated cells in-vitro or during early embryonic development in vivo. Furthermore, the increase in the expression of genes associated with primed-state pluripotency in 15% O2+2 PSI is suggestive that these cells are either poised for, or in initiation of, a transition from pluripotency to a more differentiated state.

Figure 4F:
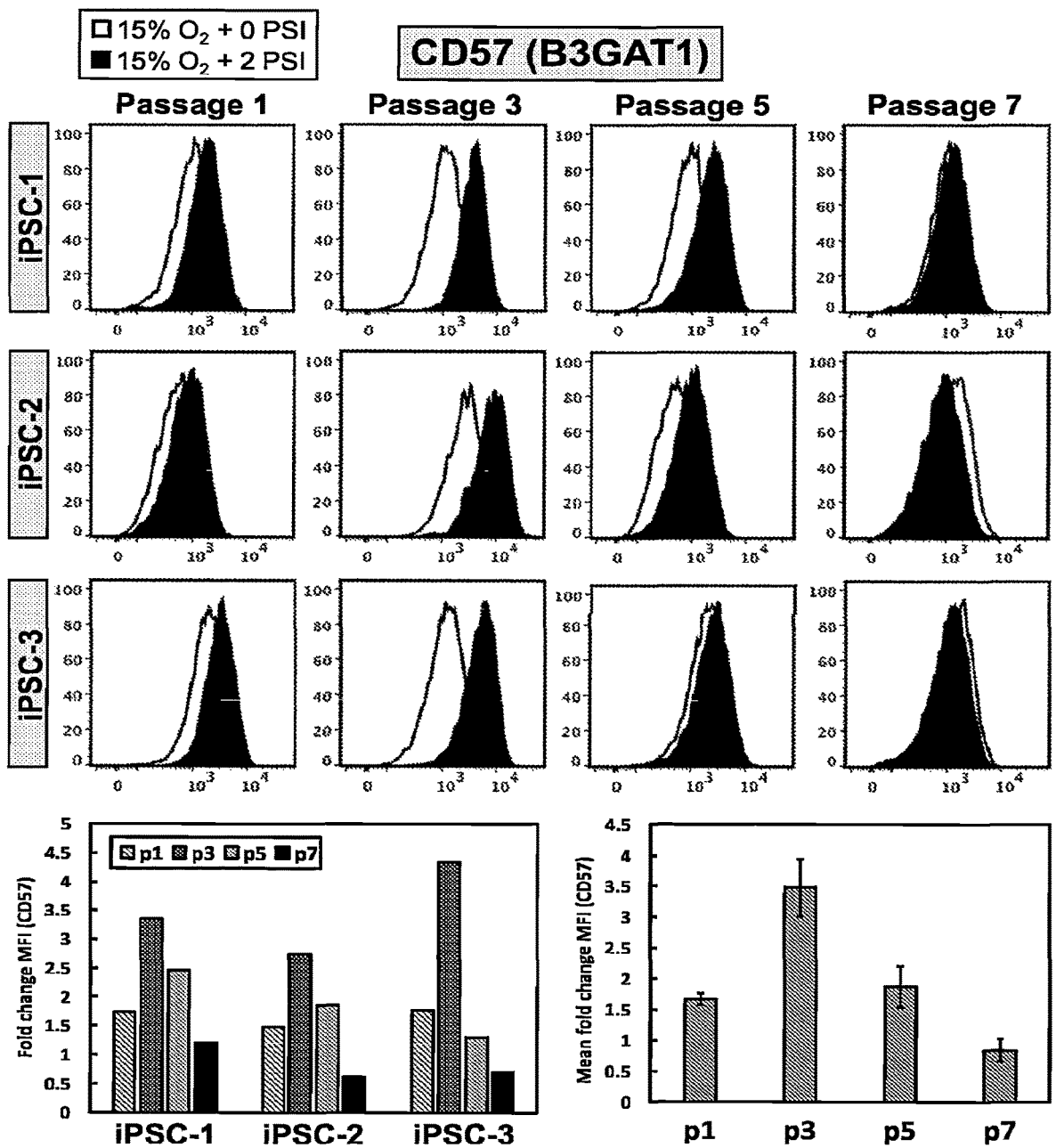

FIG. 4F shows flow cytometry analysis of iPSCs stained for the primed-state associated surface marker CD57 (B3GAT1) in the indicated culture condition. Bottom left column graph is mean fluorescence intensity (MFI, the geometric mean) for the histograms. Bottom right column graph is the mean MFI at each time-point for all iPSC lines. CD57 (B3GAT1) has been identified as a cell surface marker that is specific to primed-state pluripotency in human embryonic stem cells and iPSCs. Here the expression of CD57 is shown to increase in iPSCs cultured in 15% O2+2 PSI using immunofluorescence staining followed by flow cytometry analysis, with peak expression observed at passage 3. The reduction of CD57 back to basal levels at passage 7 may be an indication that the iPSCs have transitioned from primed-state pluripotency to a downstream phenotypic state.

Figure 5A:
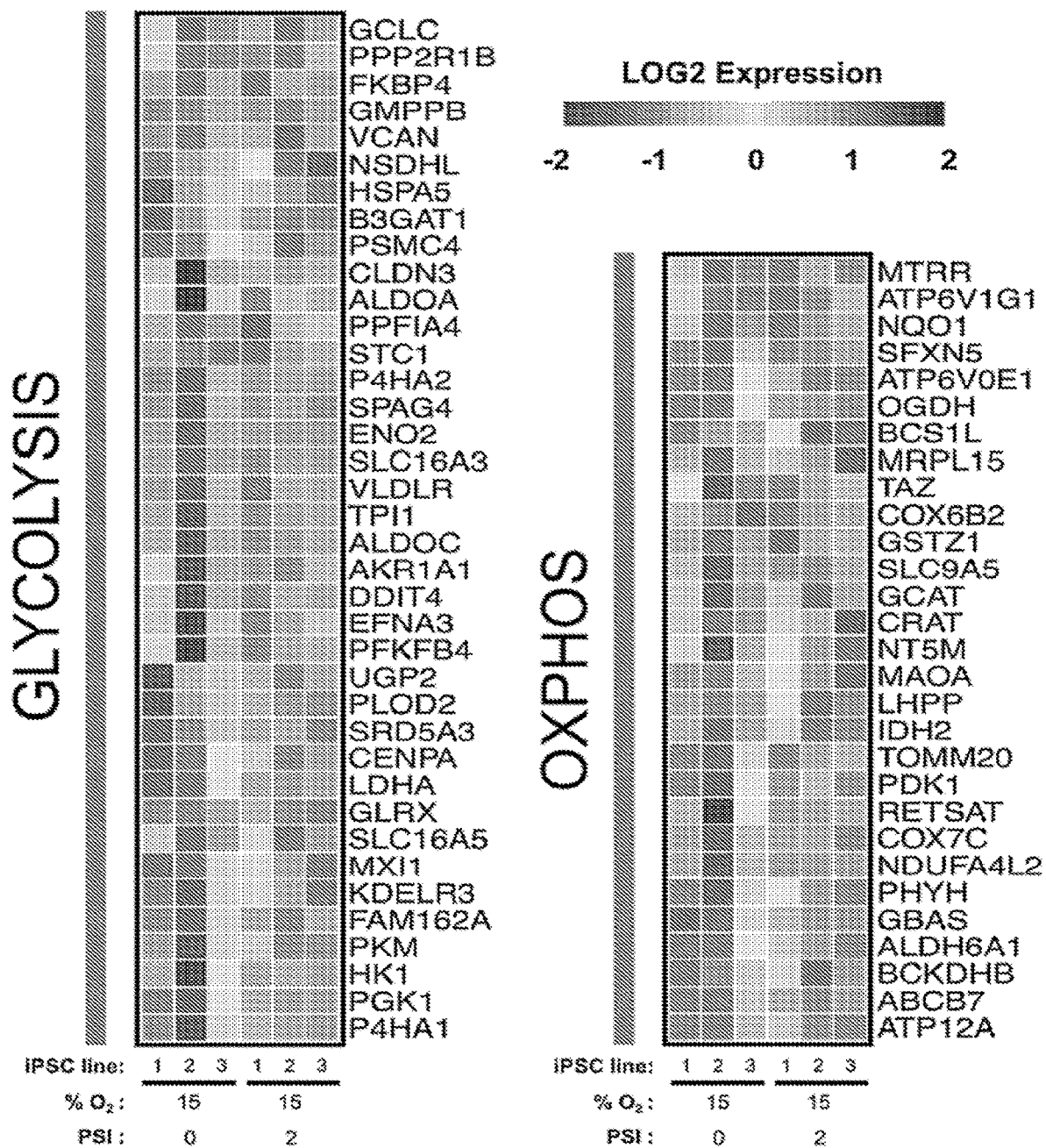
FIGS. 5A-5B show metabolic gene expression changes in response to short and long-term culture of iPSCs in 15% oxygen and increased atmospheric pressure.
Figure 5B:
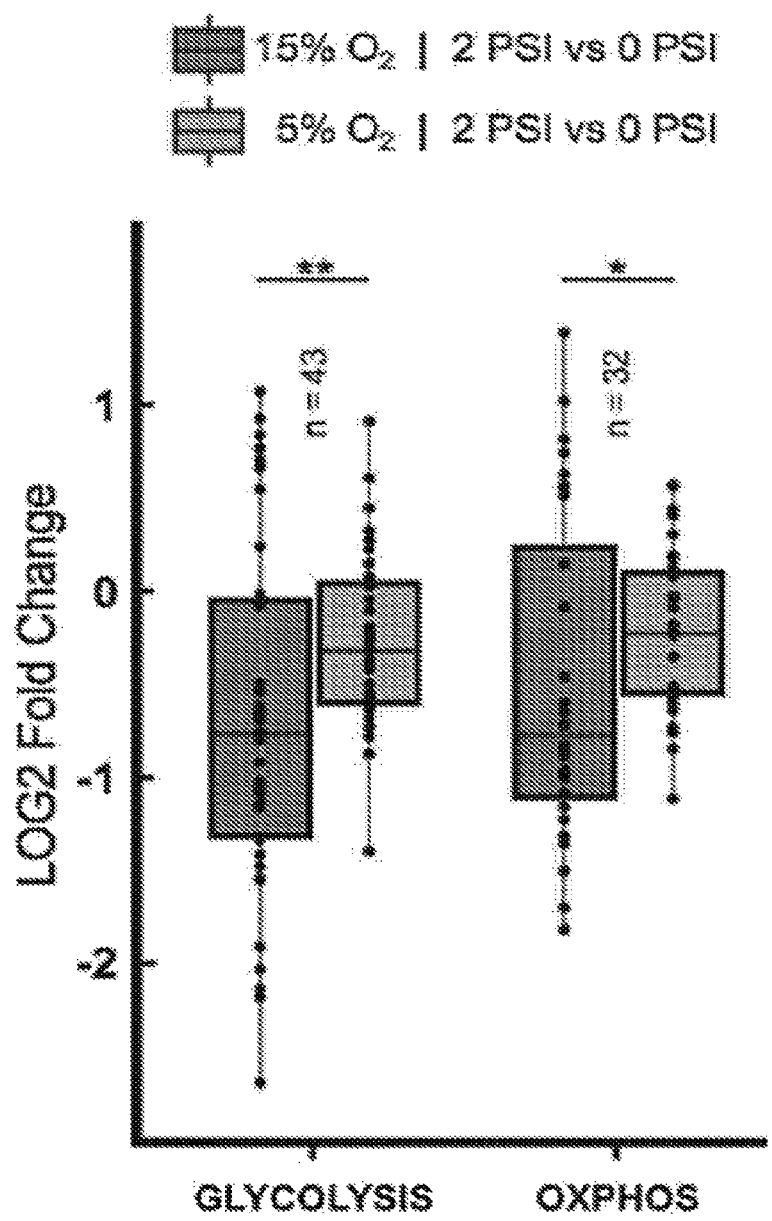

FIGS. 5A-5B show metabolic gene expression changes in response to short and long-term culture of iPSCs in 15% oxygen and increased atmospheric pressure. FIG. 5A Glycolysis and oxidative phosphorylation pathway-related genes from Hallmark and Kegg gene ontology databases that are differentially expressed between 15% O2+2 PSI vs. 15% O2+0 PSI at passage 3 with adjusted (FDR) p-value<0.05. Un-supervised hierarchical clustering of data is shown as scaled log 2 fold change across rows (genes). Genes known to regulate either glycolysis or oxidative phosphorylation metabolic pathways are differentially expressed in iPSCs cultured to passage 3 in 15% O2+2 PSI. A shift in the metabolism of iPSCs and embryonic stem cells is a feature of differentiation state or transition from naïve to primed-state pluripotency.

FIG. 5B shows box-plots of cumulative significant differentially expressed genes from (a) with 5% O2+2 PSI vs. 5% O2+0 PSI genes included. The total number of significant genes (n) is listed above each group. Box-plots representing the Log 2 fold-change in gene expression of cumulative significant differentially expressed genes for 15% O2+2 PSI vs. 15% O2+0 PSI and 5% O2+2 PSI vs. 5% O2+0 PSI analyses at passages 3 that relate to glycolysis or oxidative phosphorylation from Hallmark and Kegg gene ontology databases. At passage 3, the log 2 fold-changes in gene expression for glycolysis and oxidative phosphorylation specific genes are significantly different between 15% O2+2 PSI vs. 15% O2+0 PSI and 5% O2+2 PSI vs. 5% O2+0 PSI analyses by Wilcoxon rank-sum test, suggesting that 15% oxygen in conjunction with elevated pressure has a stronger influence on metabolic gene expression than 5% oxygen with elevated pressure.

Figure 6A:
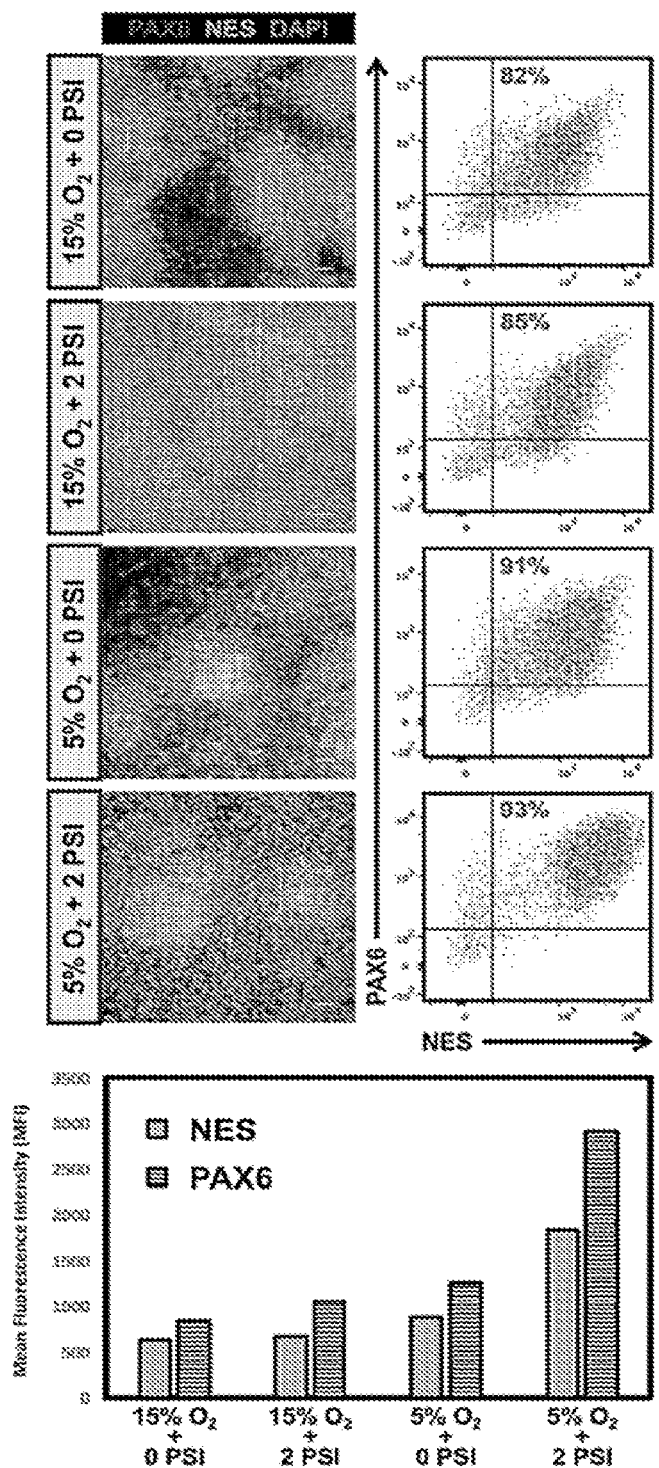
FIGS. 6A-6C show enhancement of neural induction and CNS and motor neuron differentiation and maturation under conditions of low oxygen and increased atmospheric pressure.
Figure 6B:
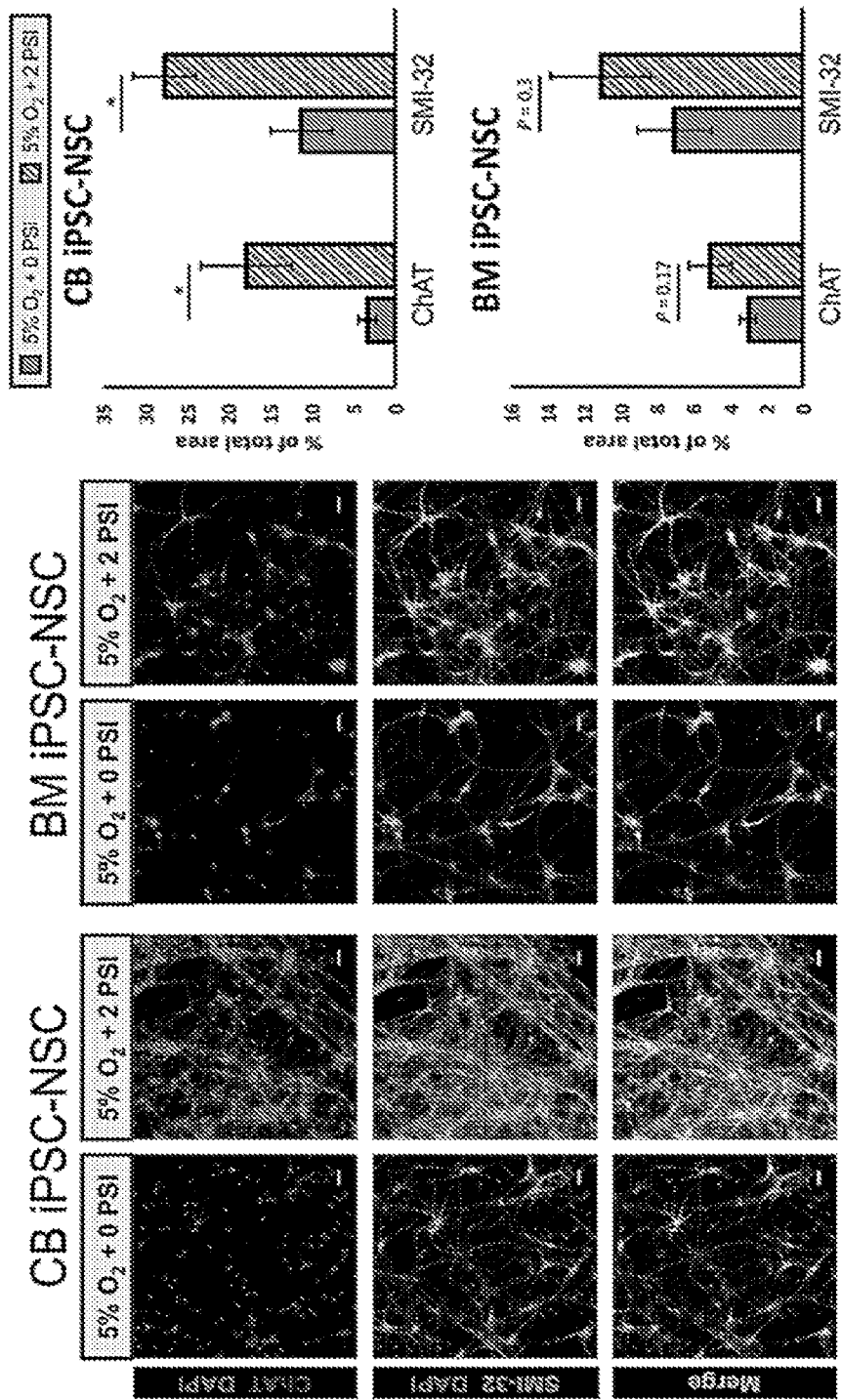
Figure 6C:
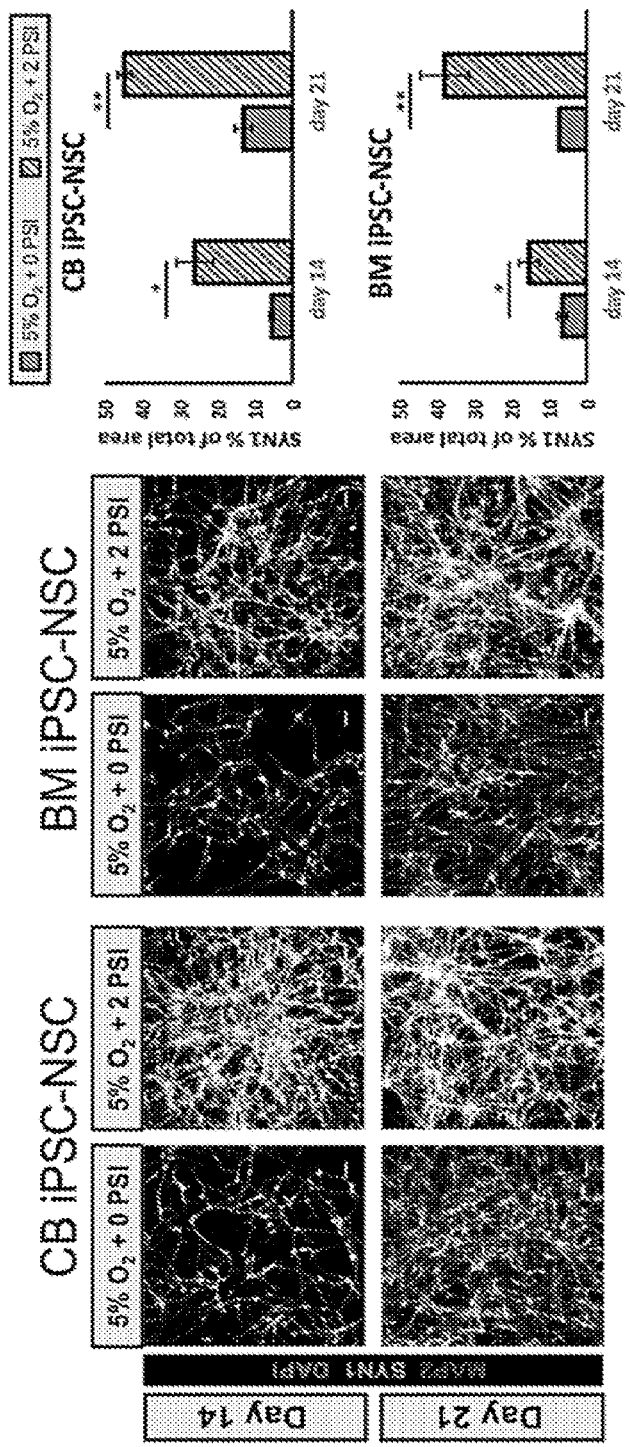

FIGS. 6A-6C show enhancement of neural induction and CNS and motor neuron differentiation and maturation under conditions of low oxygen and increased atmospheric pressure. FIG. 6A shows representative immunofluorescence images and parallel flow cytometry analysis of iPSC-2 line differentiated for 6 days in medium containing 10 ng/mL recombinant LIF and NOG and stained for markers PAX6 and NES. Bottom column graph shows geometric mean fluorescence for the flow cytometry data for PAX6 and NES. Directed differentiation using medium containing recombinant NOG and LIF can induce neural differentiation of iPSCs. Both PAX6 and NES proteins are expressed in neural progenitor cells and are common markers to identify cells within this lineage. These data show that directed differentiation of iPSC-2 line in 5% O2+2 PSI results in an increased percent of double positive PAX6 and NES expressing cells, with a concomitant increase in the mean fluorescence intensity of PAX6 and NES staining of those double positive cells.

FIG. 6B shows representative immunofluorescence images of day 31 motor neurons differentiated from cord blood derived iPSC neural stem cells (CB iPSC-NSC) and bone marrow derived iPSC neural stem cells (BM iPSC-NSC) stained for choline acetyltransferase (ChAT, in red) and neurofilament-H, as identified with antibody clone SMI-32 (in green). (Colors refer to representation in original micrographs.) Scale bars=50 μM. Quantification for ChAT and neurofilament-H is displayed in the column graphs to the right as % of total area of staining. The rationale for differentiating neural stem cells (NSCs) into motor neurons using 5% $O_2$ and elevated pressure is that these conditions showed a positive influence on neural induction in FIG. 6A. These data show that differentiation efficiency of NSCs into the motor neuron lineage under 5% O2+2 PSI in the presence of the neurotrophic factors BDNF and GDNF is increased based on choline acetyltransferase and neurofilament-H staining by immunofluorescence microscopy.

FIG. 6C shows CNS-type neuronal differentiation using the same source NSC lines as in (b) stained for both MAP2 (red) and SYN1 (green) day 14 and 21 of differentiation. Scale bars=50 μM. Quantification of the mature neuronal marker SYN1 is displayed in the column graphs to the right. For both (b) and (c), n=3 images quantified per condition. Error bars are standard error of the mean. *=p-value<0.05, **=<0.01 student's T test. The rationale for differentiating neural stem cells (NSCs) into CNS-type neurons using 5% $O_2$ and elevated pressure is that these conditions showed a positive influence on neural induction in FIG. 6A. These data show that differentiation efficiency of NSCs into the CNS-type neuron lineage under 5% O2+2 PSI is increased based on SYN1 staining by immunofluorescence microscopy. Additionally, SYN1 (Synapsin 1) is a protein expressed in mature neurons, and its expression at day 14 of differentiation specifically in 5% O2+2 PSI culture conditions suggest that the neurons are in a more mature state than their counterparts cultured in ambient atmospheric pressure.

Hematopoietic Cell Data

FIGS. 7A-7B Two unique donor iPSC lines, one from dermal fibroblasts ("F9-Xcell", in-house) and one from CD34+ cord blood cells ("NCRM5", National Institute of Health), were cultured in an Avatar™ incubator at 3% oxygen and elevated pressure (+2 PSI) for the first six days of differentiation in phase I medium, followed by culture in 15% oxygen and elevated pressure (+2 PSI) for a further 8 days in phase II medium. Cells were stained with propidium iodide to assess viability and hematopoietic stem cell markers CD34, CD43, and CD45 at the end of phase II medium incubation (14 days total differentiation) to examine the percent triple positive using the gating strategy described in the figure. The population of cells highlighted by a circle with an arrow in the far right plot identifies a CD34+ CD43$^{med}$CD45$^{high}$ lineage that is specifically enriched in the Avatar™ incubator using the variable oxygen and elevated pressure culture strategy described above. "Standard" refers to a conventional $CO_2$ incubator set to 5% $CO_2$, 37 degrees Celsius, and ambient oxygen. Error bars in the column graph are standard error of the mean for technical duplicates.

FIG. 7A shows representative flow cytometry density plots for propidium iodide and SSC-A gating, CD34 and CD43 gating, CD34 and CD45 gating, and CD34, CD43, and CD45 gating. The population of cells highlighted by a circle with a check mark in the far right plot indicates CD34+CD43$^{med}$CD45$^{high}$ expression. The hematopoietic lineage markers CD34, CD43, and CD45 are used in combination to identify cells that are differentiating towards a common lymphocyte and myeloid progenitor cell population. These data show that specific oxygen and atmospheric pressure conditions can influence the expression of CD43 and CD45 by enriching for a population of cells displaying CD34+CD43$^{med}$CD45$^{high}$ expression. In this experiment, cells were incubated in 3% O2+2 PSI for the first 6 days of differentiation (phase I), followed by incubation in 15% O2+2 PSI for another 8 days of differentiation (phase II), at which point the cells were stained for CD34, CD43, and CD45 and analyzed by flow cytometry. These results highlight how oxygen and atmospheric pressure can influence the phenotypic state during hematopoietic stem cell differentiation in a 2-phase process.

FIG. 7B is a bar graph showing mean percent of CD34+ CD43medCD45+ expressing cells for each iPSC line from the flow cytometry data of FIG. 7A. Error bars in the column graph are standard error of the mean for technical duplicates. For FIGS. 7A and 7B, "standard" refers to a conventional $CO_2$ incubator set to 5% $CO_2$, 37 degrees Celsius, and ambient oxygen. This graph summarizes the data in FIG. 7A as mean percent of total live cells (propidium iodide negative) with CD34+CD43$^{med}$CD45$^{high}$ expression across the two unique donor iPSC lines (F9-Xcell and NCRM5) used for this hematopoietic stem cell differentiation experiment.

Method Flow Diagram for Embodiment 1

FIG. 8 is a flow diagram of an embodiment of a method of modulating the potency level phenotype of a cell population by regulating one or more variable aspects of a gaseous condition within an incubator such that these gaseous conditions differ from the corresponding ambient gaseous condition. Aspects of this method embodiment are detailed in the "Summary of the Present disclosure", above. A conceptual basis of this method is shown in FIGS. 1A, 1B, and 2. Illustrative examples of scientific support for embodiments of this method with various types of cells are shown in FIGS. 3A-7B. FIGS. 8-12 provide flow diagrams of further embodiments of methods provided by the present disclosure.

In brief (FIG. 8), steps of this embodiment of the present disclosure include (step 801) culturing a cell population in an incubator able to regulate one or more variable parameters of a gaseous condition within the incubator independently of a corresponding ambient gaseous condition, and (step 802) regulating the one or more variable parameters of the gaseous condition within the incubator such that at least one of the one or more variable parameter differs from an ambient level of the variable parameter, and as a consequence of such difference from ambient conditions, driving the subset population from a first potency level phenotype to a second potency level phenotype.

Modulating a Phenotype with by Application of Uniformly Distributed Pressure

In addition to the embodiments of a method of modulating cell potency-level phenotype by way of regulating the gaseous environment within a cell culture incubator, as described above in the "Summary of the Present disclosure" and in the "Detailed Description" sections, further embodiments are provided. Each of the embodiments that follow may include any aspect of first embodiment as described herein.

In a second embodiment, among several exemplary embodiments provided herein, an embodiment of the present disclosure is represented in FIG. 9.

FIG. 9 is a flow diagram of a method 900 of modulating the potency level phenotype of a cell population by regulating one or more variable aspects of a gaseous condition within an incubator such that these gaseous conditions differ from the corresponding ambient gaseous condition, wherein the pressure is application substantial uniformity across the cell surface. In brief, this embodiment of the present disclosure includes 901 culturing a cell population in an incubator able to regulate one or more variable parameters of a gaseous condition within the incubator independently of a corresponding ambient gaseous condition, and 902 controlling a pressure exerted on cells within the cell population, wherein the pressure is greater than ambient atmospheric pressure, and wherein the pressure is distributed with substantial uniformity across a surface of each cell, consequently driving the subset population from a first potency level phenotype to a second potency level phenotype.

Aspects of the method shown in FIG. 9 will now be elaborated in further detail. In some embodiments of the present disclosure, pressure, as one of the atmospheric variables, is characterized particularly as exerting its biological effects on cells in a manner that is uniformly distributed across the cell surface area. Accordingly, some embodiments of a method of modulating a cellular potency level phenotype of at least a subset population of a source population of cells include culturing the source cell population in a liquid medium within a cell culture incubator; and (among atmospheric variables) controlling a pressure exerted on cells of the cell population, wherein the pressure is greater than ambient atmospheric pressure, and wherein the pressure is distributed with substantial uniformity across a surface of each cell. By virtue of exerting uniformly distributed pressure, the method further includes driving the subset population from a first potency level phenotype to a second potency level phenotype, wherein the first potency level phenotype of the subset cell population is that which would be expressed under a gaseous condition in which total atmospheric pressure is at an ambient level, and wherein the second potency level phenotype of the subset cell population is expressed as a consequence of exposure to the pressure higher than that of ambient atmospheric pressure.

In particular embodiments of this method, the pressure exerted on the cells is distributed across substantially every portion of the surface of each cell with a substantially identical time course. These embodiments may further include controlling a concentration of oxygen in the cell culture incubator such that the concentration within the incubator is lower than the ambient oxygen concentration;

and wherein the second potency level phenotype of the subset population is expressed, at least in part, as a consequence of exposure to the concentration of oxygen being less than that of the ambient level.

Modulating a Phenotype: First to Second, Second to Third

In a third embodiment, among several exemplary embodiments provided herein, an embodiment of the present disclosure is represented in FIG. 10.

FIG. 10 is a flow diagram of a method 1000 of modulating the potency level phenotype of a cell population through multiple potency levels by regulating one or more variable aspects of a gaseous condition within an incubator such that these gaseous conditions differ from the corresponding ambient gaseous condition.

In brief, this embodiment of the present disclosure includes 1001 culturing a cell population in an incubator able to regulate one or more variable parameters of a gaseous condition independently of a corresponding ambient gaseous condition. The method further includes (1002) regulating each of the one or more variable parameters of the gaseous conditions within the incubator independently of the ambient gaseous condition, and consequently and sequentially driving the subset population from a first potency level phenotype to a second potency level phenotype, and then from the second potency level phenotype to a third potency level phenotype.

Aspects of the method shown in FIG. 10 will now be elaborated in further detail. Some embodiments of the present disclosure include moving a subject cell population from a first to a second potency level phenotype, and them moving the second potency level phenotype to a third potency level phenotype. Accordingly, in some embodiments of the present disclosure, a method of modulating a potency level phenotype of at least a subset population of a source population of cells, the method includes culturing the source cell population in a liquid medium within a cell culture incubator, the incubator configured to independently regulate one or more variable parameters of gaseous conditions within the incubator; and regulating each of the one or more variable parameters of the gaseous conditions within the incubator independently of each other and independently of an ambient external gaseous condition. By virtue of regulating the one or more atmospheric variables, the method then includes driving the subset population from a first potency level phenotype to a second phenotype, and thence from the second potency level phenotype to a third potency level phenotype.

In this embodiment, the first potency level phenotype of the subset cell population is expressed under a culture condition the one or more variable parameters of the gaseous condition are substantially in accordance with ambient conditions (a first set of gaseous conditions), and the second potency level phenotype of the subset cell population is expressed as a consequence of exposure to a second set of gaseous conditions as determined by the independent regulation of the one or more parameters of the gaseous conditions within the incubator, and the third potency level phenotype of the subset cell population is expressed as a consequence of exposure to a third set of gaseous conditions as determined by the independent regulation of the one or more parameters of the gaseous conditions within the incubator. In some of these embodiments, one of the variable aspects of the gaseous conditions within the incubator is a total gas pressure, and wherein a second of the variable aspects of the gaseous conditions within the incubator is a concentration of oxygen.

In one example of this embodiment, the source population includes fibroblasts derived from a human being, such fibroblasts are of a first potency level phenotype, and the second potency level phenotype is that of an induced pluripotent stem cell (iPSC), and the third potency level phenotype is that of an intermediately differentiated cell. In some of these particular embodiments, driving the subset of the source population toward the second potency level phenotype (the iPSC) includes including one or more transcription factors in the cell culture medium. In some embodiments, the source population of fibroblasts is derived from a donor human being, by way of a skin biopsy, the donor being be any of a fetus, a neonate, an infant, a child, an adolescent, or an adult.

Some embodiments of this method of deriving second and third potency level phenotypes from a first potency level phenotype, include expanding the cultured subset of cells of expressing the third potency level phenotype by culturing under the second set of gaseous conditions.

Modulating a Phenotype: A Manufacturing Process Context, with Particular Modules and Work Flows In a fourth embodiment, among several exemplary embodiments provided herein, an embodiment of the present disclosure is represented in FIG. 11.

FIG. 11 is a flow diagram of a method 1100 of modulating the potency level phenotype of a cell population within a workflow context that may be used in a clinical manufacturing context, where an expanded cell population of a particular potency level phenotype may be used for research, diagnostic, drug screening, or therapeutic purposes. In brief, this embodiment of the method includes 1101 culturing a source cell population in an incubator capable of operating multiple gaseous condition modules, including a module A for pluripotency, a module B for intermediate potency level, and a module C for a differentiated potency level, each module delivering a particular oxygen level and a total gas pressure within the cell culture incubator. The method further includes 1102 regulating oxygen level and total gas pressure within the incubator in accordance with the gaseous condition module that favors the targeted potency level phenotype. Embodiments of the method further include 1103 culturing the cell population and the appropriate module conditions to expand a population of cells having the targeted potency level phenotype.

Aspects of the method shown in FIG. 11 are depicted in general terms in FIG. 2, and will now be elaborated on in further detail. Some embodiments of the present disclosure include adapting the method to a clinical manufacturing process context, with particular modules and work flows 1100. Accordingly, a method of modulating phenotypic potency level to achieve a targeted level of phenotypic potency level, includes 1101 culturing a source cell population in a liquid medium within a cell culture incubator that is capable of operating multiple gaseous condition modules, the modules including a condition module A for pluripotency, a condition module B for intermediate potency level, and a module C for a differentiated potency level, wherein each module operates at a specification with regard to oxygen level and total gas pressure conditions within the cell culture incubator. The method further includes 1102 regulating oxygen level and total gas pressure within the incubator in accordance with the gaseous condition module that favors the targeted potency level phenotype; and further culturing 1103 the cell population and the appropriate module conditions to expand a population of cells having the targeted potency level phenotype.

In some embodiments of the method, prior to regulating oxygen level and total gas pressure within the incubator in accordance with the gaseous condition module that favors the targeted potency level phenotype, regulating gaseous conditions in accordance with one of the other gaseous condition modules.

In some embodiments of the method, further culturing the cell population includes culturing in a workflow that comprises at least two consecutive culture condition modules.

In some embodiments of the method, the gaseous condition module that favors the targeted potency level phenotype is based on any of experimental data from previous examples of a population of cells of a same type as the source population or from previous examples of populations of cells similar to those of the source population.

Modulating Phenotype with Two or More Gaseous Parameter Variables

In a fifth embodiment, among several exemplary embodiments provided herein, an embodiment of the present disclosure is represented in FIG. 12.

FIG. 12 is a flow diagram of a method 1200 an embodiment of a method of modulating a cellular phenotype of at least a subset population of a source population of cells includes culturing 1201 the source cell population in a liquid medium within a cell culture incubator, the incubator being configured to regulate two or more variable parameters of gaseous conditions within the incubator independently of each other and independent of a corresponding ambient condition. Embodiments of the method include regulating 1201 the two or more variable parameters of the gaseous condition within the incubator such that at least two of the two or more variable parameter differs from a corresponding ambient level, and consequently driving the subset population from a first phenotype to a second phenotype. In these method embodiments, the first phenotype of the subset cell population is that which is expressed under a gaseous condition absent the independent regulation of the two or more variable parameters of the gaseous condition, and the second phenotype of the subset cell population is expressed as a consequence of exposure to the gaseous condition as determined by the independent regulation of the two or more parameters of the gaseous conditions within the incubator.

In some of these embodiments, the source cell population includes cell populations selected from the group consisting of immune cells, tumor cells, and stem cells. In particular examples of these embodiments, the immune cell populations may include monocytes, macrophages, antigen-presenting cells, dendritic cells, T-cells, Tumor-infiltrating T cells, Regulatory T cells, NK cells, neutrophils, and B-cells. In other embodiments, stem cells may include naturally occurring stem cells or induced stem cells. Stem cell populations may include mesenchymal stem cells, said mesenchymal stem cells including any of progenitor, immature and mature subgroups.

In some of these embodiments, the second phenotype (in contrast to the initial or "first" phenotype) is a desired type of cell in a desired phenotypic state, the desired phenotypic state including a desired functionality. In one such example, the source population is an induced pluripotent stem cell (iPSC) population and the desired type of cell is a mature natural killer (NK) cell that has functional tumor-killing properties, such desired cells being appropriate to deploy in immuno-oncology applications. In particular embodiments, the mature natural killer (NK) cell with functional tumor-killing properties has a range of tumor-killing levels, and relevantly, regulating the two or more variable parameters of the gaseous condition within the incubator can modulate the level of tumor-killing efficacy. In some of these embodiments, the desired type of cell is a mature immune cell in which one or more of the immune markers identifying an aspect of the "self" of the source population have been removed, the desired cell type thereby becoming a universal donor cell.

In some embodiments of the present disclosure, one of the variable parameters of the gaseous conditions within the incubator is a total gas pressure, the total gas pressure is greater than ambient total gas pressure. In some embodiments of the present disclosure, one of the variable parameters of the gaseous conditions within the incubator is a concentration of an individual gas. In a particular embodiment, the individual gas is oxygen, and the level of oxygen is below ambient oxygen level.

Any one or more features or steps of any embodiment of the present disclosures disclosed herein (device or method) can be combined with any one or more other features of any other embodiment of the present disclosures, without departing from the scope of the present disclosure. It should also be understood that the present disclosures are not limited to the embodiments that are described or depicted herein for purposes of exemplification, but are to be defined only by a fair reading of claims appended to the patent application, including the full range of equivalency to which each element thereof is entitled. Some theoretical considerations of the inventors have been advanced in this application, as, for example, regarding the biological effects of oxygen level and atmospheric pressure on cells. These theoretical considerations are offered strictly for the purpose of conveying concepts underlying the present disclosures, not to support any of the claims, all of which stand wholly independent of any theoretical considerations.

EMBODIMENTS

The following non-limiting embodiments provide illustrative examples of the invention, but do not limit the scope of the invention.

Embodiment 1. A method of modulating a potency level phenotype of at least a subset population of a source population of cells, the method comprising: culturing the source cell population in a liquid medium within a cell culture incubator, the incubator configured to to regulate one or more variable parameters of a gaseous condition within the incubator independently of an ambient gaseous condition; regulating the one or more variable parameters of the gaseous condition within the incubator such that at least one of the one or more variable parameter differs from an ambient level of the variable parameter, and as a consequence of such difference from ambient conditions, the subset population is driven from a first potency level phenotype to a second potency level phenotype, wherein the first potency level phenotype of the subset cell population is that which is expressed under a gaseous condition in which the one or more variable gaseous parameters are substantially in accordance with ambient conditions, and wherein the second potency level phenotype of the subset cell population is expressed as a consequence of exposure to the gaseous condition as determined by the regulation of the one or more parameters of the gaseous conditions within the incubator.

Embodiment 2. The method of embodiment 1, wherein one of the variable parameters of the gaseous conditions within the incubator is a total gas pressure, and wherein the total gas pressure is greater than ambient total gas pressure.

Embodiment 3. The method of embodiment 1, wherein one of the variable parameters of the gaseous conditions within the incubator is a concentration of an individual gas.

Embodiment 4. The method of any one of embodiments 1-3, wherein the individual gas is oxygen, and wherein the level of oxygen is below ambient oxygen level.

Embodiment 5. The method of any one of embodiments 1-4, wherein the incubator is configured to regulate two or more variable parameters of a gaseous condition within the incubator independently of an ambient gaseous condition, and configured to regulate the two or more variables of a gaseous condition independently of each other.

Embodiment 6. The method of embodiment 5, wherein one of the two variable parameters comprises a total gas pressure and wherein a second of the two variable parameters comprises an oxygen level.

Embodiment 7. The method of embodiment 5, wherein the two or more variable parameters of the gaseous conditions comprise a total gas pressure and a concentration of at least one individual gas, and wherein culturing the cells within a cell culture incubator comprises culturing for a culture duration over which time both the total gas pressure and the concentration of the at least one gas is substantially constant.

Embodiment 8. The method of embodiment 5, wherein the two or more variable parameters of the gaseous conditions comprise a total gas pressure and a concentration of at least one individual gas, and wherein culturing the cells within a cell culture incubator comprises varying at least one of the total gas pressure or the concentration of the at least one gas over a culture duration.

Embodiment 9. The method of any one of embodiments 1-8, wherein modulating the phenotype comprises modulating a potency level aspect of the phenotype of the subset population of cultured cells such that the first phenotype and the second phenotype differ with regard to potency level.

Embodiment 10. The method of embodiment 9, wherein modulating the potency level aspect of the phenotype of the subset population of cultured cells comprises driving the cells from a state of high potency level toward a state of a mature, differentiated cell phenotype.

Embodiment 11. The method of embodiment 9, wherein modulating a potency level phenotype comprises driving a cell having a pluripotent phenotype toward a cell type belonging to any of the embryonic germ layer derivatives, said germ layers consisting or endoderm, mesoderm, and ectoderm.

Embodiment 12. The method of embodiment 11, wherein driving a phenotype toward an ectodermal derived cell type comprises driving the phenotype toward that of an ectodermal or neural cell type.

Embodiment 13. The method of embodiment 9, wherein modulating a potency level phenotype comprises driving a cell having a pluripotent phenotype toward that of an intermediately differentiated or progenitor cell phenotype.

Embodiment 14. The method of embodiment 10, wherein driving a phenotype toward a state of a mature, differentiated cell type comprises driving a population human induced pluripotent cells (iPSCs) toward a myeloid progenitor cell type, as indicated by emergence of CD34+CD45+CD43+ cells.

Embodiment 15. The method of any one of embodiments 1-14, wherein modulating a potency level phenotype comprises driving a cell having an intermediately differentiated cell phenotype toward that of a cell having fully differentiated cell phenotype.

Embodiment 16. The method of embodiment 15, wherein an intermediately differentiated cell phenotype comprises a neural cell phenotype and a mature differentiated call phenotype comprises a neuronal phenotype.

Embodiment 17. The method of embodiment 9, wherein modulating the potency level aspect of the phenotype of the subset population of cultured cells comprises driving the cells from a differentiated state toward a state of higher potency.

Embodiment 18. The method of embodiment 15, wherein modulating a differentiation phenotype comprises driving a cell having differentiated cell phenotype toward an induced pluripotent stem cell (iPSC) phenotype.

Embodiment 19. The method of any one of embodiments 1-18, further comprising modulating the second phenotype such that it becomes a third phenotype.

Embodiment 20. The method of any one of embodiments 1-19, wherein modulating the potency level phenotype comprises modulating an expression of a differentiation marker, said marker reflecting any or more of gene expression, protein expression, cellular functionality, kinetic property, or metabolic pathway activity of at least the subset population of the cultured population of primary cells.

Embodiment 21. The method of embodiment 20, wherein the differentiation marker comprises a neural cell marker.

Embodiment 22. The method of any one of embodiments 1-21, wherein modulating a state of potency-level phenotype comprises modulating an expression of an aspect of cell morphology, dimension, adherent properties, migratory behavior, electrical, activation, or functional properties of at least the subset population of the cultured population of primary cells.

Embodiment 23. The method of any one of embodiments 1-22, wherein the liquid medium comprises one or more cell differentiation induction factors or growth factors.

Embodiment 24. The method of any one of embodiments 1-23, further comprising isolating cells of the second phenotype, and expanding a population of cells of the second phenotype by way of further cell culturing.

Embodiment 25. The method of embodiment 24, wherein a particular second phenotype is desired, and wherein a set of the two or more independently regulated parameters of the gaseous conditions that favor an expression of the desired second phenotype has been determined, the method further comprising expanding the cultured subset of cells of expressing the second phenotype by a culturing under those independently regulated gaseous conditions.

Embodiment 26. The method of any one of embodiments 1-25, wherein the method is adapted to determine a gaseous condition favorable for outgrowth of a population having a desired phenotype, the method comprising: splitting the source population of cells into cohort cultures comprising at least a first and a second cohort culture; culturing the cohort cell cultures in parallel under gaseous conditions that differ only with regard for variations in any of total gas pressure and oxygen concentration; measuring a level of an expression of at least one marker indicative of the desired phenotype within each of the cohort cultures; and based on the results of differentiation marker level measurement among the cohort cultures, determining which of the variations in gaseous conditions is optimal for the outgrowth of the cell population having the desired phenotype.

Embodiment 27. A method of modulating a phenotype of at least a subset population of a source population of cells, the method comprising: culturing the source cell population in a liquid medium within a cell culture incubator, the incubator configured to regulate two or more variable parameters of a gaseous condition within the incubator independently of a corresponding ambient gaseous condition; regulating the two or more variable parameters of the gaseous condition within the incubator such that each of the variable parameters differs from a respective ambient level, and consequently driving the subset population from a first phenotype to a second phenotype, wherein the first phenotype of the subset cell population is that which is expressed under a gaseous condition in which the two or more variable gaseous parameters are substantially in accordance with ambient conditions, and wherein the second phenotype of the subset cell population is expressed as a consequence of exposure to the gaseous condition as determined by the regulation of the two or more parameters of the gaseous conditions within the incubator.

What is claimed is:

1. A method of modulating a cellular morphology of at least a subset of a source population of cells, in a cell culture incubator the method comprising:
   culturing the source population of cells having a first morphology in a medium within the cell culture incubator, wherein the first morphology presents at a first oxygen level;
   regulating the first oxygen level in the incubator to a first set oxygen level, wherein the first set oxygen level differs from the first oxygen level;
   regulating a total gas pressure level in the incubator to a first set pressure level greater than 14.69 psi;
   inducing a change in the first morphology of the subset of the source population of cells to a second morphology;
   wherein the first morphology is an initial morphology of the population of cells, and
   wherein the second morphology differs from the first morphology, and
   wherein the incubator is configured to regulate the oxygen level in the incubator and the total gas pressure level in the incubator independently of each other.

2. The method of claim 1, wherein the inducing the change in the first morphology to the second morphology occurs due to at least one of regulating the first oxygen level to the first set oxygen level, or regulating the total gas pressure level to the first set pressure level.

3. The method of claim 2, wherein the inducing the change in the first morphology to the second morphology occurs due to both regulating the first oxygen level to the first set oxygen level, and regulating the total gas pressure level to the first set pressure level.

4. The method of claim 1, further comprising regulating the first set oxygen level to a second set oxygen level.

5. The method of claim 4, wherein the population of cells is driven from the first morphology to a second morphology due to the regulating the first set oxygen level to the second set oxygen level.

6. The method of claim 4, further comprising inducing a change in the second morphology to a third morphology, wherein the third morphology differs from the second morphology.

7. The method of claim 6, wherein the population of cells is driven from the second morphology to the third morphology due to the regulating the first set oxygen level to the second set oxygen level.

8. The method of claim 1, wherein the first set oxygen level simulates a hypoxic extracellular environment.

9. The method of claim 1, wherein the first oxygen level corresponds to a nonhypoxic oxygen level, an oxygen level greater than or equal to 19.5% w/w oxygen, or an oxygen level of about 21% w/w oxygen.

10. The method of claim 8, wherein the hypoxic oxygen level is below 19.5% w/w oxygen.

11. The method of claim 1, wherein the first set pressure level exceeds 14.7 psia.

12. The method of claim 1, further comprising regulating the first set pressure level to a second set pressure level.

13. The method of claim 1, wherein the population of cells comprises stem cells or a population stem cells for a cell-based therapy.

14. The method of claim 1, wherein the population of cells is derived from a hematopoietic stem cell lineage.

15. The method of claim 1, wherein the first oxygen level is greater than or equal to 19.5% oxygen.

16. The method of claim 1, wherein the inducing the change in the first morphology to the second morphology comprising differentiating the subset of the source population of cells.

17. The method of claim 16, wherein the differentiation occurs due to at least one of regulating the first oxygen level to the first set oxygen level, or regulating the total gas pressure level to the first set pressure level.

18. The method of claim 1, wherein the first morphology and the second morphology differ in phenotype.

19. A method of modulating a cell phenotype of a subset population of cells within a source population of cells, the method comprising:
   culturing the source population of cells having a first cell phenotype in a medium within a cell culture incubator;
   regulating an oxygen level in the incubator to a set oxygen level;
   regulating a concentration level of a second gas in the incubator to a set second gas concentration level;
   regulating a total gas pressure level in the incubator to a set pressure level greater than 14.69 psi,
   wherein the oxygen level in the incubator and the total gas pressure level in the incubator are regulated independently of each other,
   wherein the subset population of cells is driven from the first cell phenotype to a second cell phenotype due to at least one of the set oxygen level in the incubator, the set second gas concentration level, or the pressure level within the incubator,
   wherein the first cell phenotype of the subset cell population is an initial cell phenotype of the source population of cells, and
   wherein the second cell phenotype of the subset cell population differs from the first cell phenotype.

* * * * *